US011342045B2

(12) United States Patent
Gao et al.

(10) Patent No.: US 11,342,045 B2
(45) Date of Patent: May 24, 2022

(54) METHOD FOR DETERMINING HETEROLOGOUS BIOSYNTHESIS PATHWAYS

(71) Applicant: King Abdullah University of Science and Technology, Thuwal (SA)

(72) Inventors: Xin Gao, Thuwal (SA); Hiroyuki Kuwahara, Thuwal (SA); Meshari Saud Alazmi, Thuwal (SA); Xuefeng Cui, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 996 days.

(21) Appl. No.: 16/067,687

(22) PCT Filed: Feb. 2, 2017

(86) PCT No.: PCT/IB2017/050576
§ 371 (c)(1),
(2) Date: Jul. 2, 2018

(87) PCT Pub. No.: WO2017/134602
PCT Pub. Date: Aug. 10, 2017

(65) Prior Publication Data
US 2019/0018922 A1    Jan. 17, 2019

Related U.S. Application Data

(60) Provisional application No. 62/291,308, filed on Feb. 4, 2016.

(51) Int. Cl.
*G16B 5/30*    (2019.01)
*G16B 5/00*    (2019.01)
(Continued)

(52) U.S. Cl.
CPC ............... *G16B 5/30* (2019.02); *G16B 5/00* (2019.02); *G16B 45/00* (2019.02); *G16B 30/00* (2019.02); *G16B 35/00* (2019.02); *G16C 20/60* (2019.02)

(58) Field of Classification Search
CPC .......... G16B 5/00; G16B 45/00; G16B 99/00; G16B 30/00; G16B 5/30; G16B 35/00; G16C 20/60
See application file for complete search history.

(56) References Cited

U.S. PATENT DOCUMENTS

2005/0079482 A1*   4/2005   Maranas ................. G16B 5/00
435/4

OTHER PUBLICATIONS

Adam Arkin et al., "Stochastic Kinetic Analysis of Developmental Pathway Bifurcation in Phage λ-Infected *Escherichia coli* Cells", Genetics, Aug. 1998, pp. 1633-1648, vol. 149.
(Continued)

*Primary Examiner* — Jesse P Frumkin
(74) *Attorney, Agent, or Firm* — Patent Portfolio Builders PLLC

(57) ABSTRACT

The present invention relates to a method and system for dynamically analyzing, determining, predicting and displaying ranked suitable heterologous biosynthesis pathways for a specified host. The present invention addresses the problem of finding suitable pathways for the endogenous metabolism of a host organism because the efficacy of heterologous biosynthesis is affected by competing endogenous pathways. The present invention is called MRE (Metabolic Route Explorer), and it was conceived and developed to systematically and dynamically search for, determine, analyze, and display promising heterologous pathways while considering competing endogenous reactions in a given host organism.

10 Claims, 15 Drawing Sheets

(51) Int. Cl.
G16B 45/00 (2019.01)
G16B 30/00 (2019.01)
G16B 35/00 (2019.01)
G16C 20/60 (2019.01)

(56) References Cited

OTHER PUBLICATIONS

Amos Bairoch, "The ENZYME database in 2000", Nucleic Acids Research, 2000, pp. 304-305, vol. 28, No. 1.
Anne Morgat et al., "Updates in Rhea—a manually curated resource of biochemical reactions", Nucleic Acids Research, 2015, pp. D-459-D464, vol. 43.
Avi Flamholz et al., "eQuilibrator—the biochemical thermodynamics calculator", Nucleic Acids Research, 2012, pp. D770-D775, vol. 40.
C.J. Paddon et al., "High-level semi-synthetic production of the potent antimalarial artemisinin", Nature, Apr. 2013, pp. 528-536, vol. 496.
Cesar A.G. Quispe et al., "Glycerol: Production, consumption, prices, characterization and new trends in combustion", Renewable and Sustainable Energy Reviews, 2013, pp. 475-493, vol. 27.
Chih-Hung Chou et al., "FMM: a web server for metabolic pathway reconstruction and comparative analysis", Nucleic Acids Research, 2009, pp. W129-W134, vol. 37.
Chris J. Paddon et al., "Semi-synthetic artemisinin: a model for the use of synthetic biology in pharmaceutical development", Microbiology, Nature Reviews, May 2014, pp. 355-367, vol. 12.
Christine Nicoel S. Santos et al., "Optimization of a heterologous pathway for the production of flavonoids from glucose", Metabolic Engineering, 2011, pp. 392-400, vol. 13.
Collin H. Martin et al., "Synthetic Metabolism: Engineering Biology at the Protein and Pathway Scales", Chemistry & Biology Review, Mar. 2009, pp. 277-286, vol. 16.
Dae-Kyun Ro et al., "Production of the antimalarial drug precursor artemisinic acid in engineered yeast", Nature, Apr. 2006, pp. 940-943, vol. 440.
Effendi Leonard et al., "Strain Improvement of Recombinant *Escherichia coli* for Efficient Production of Plant Flavonoids", Molecular Pharmaceutics, 2008, pp. 257-265, vol. 5, No. 2.
Eunyoung Jeon et al., "Development of a *Saccharomyces cerevisiae* strain for the production of 1,2-propanediol by gene manipulation", Enzyme and Microbial Technology, 2009, pp. 42-47, vol. 45.
Gary K. Ackers et al., Quantitative model for gene regulation by λ phage repressor, Proc. Natl. Acad. Sci. USA, Feb. 1982, pp. 1129-1133, vol. 79.
Gert Forkmann et al., "Metabolic engineering and applications of flavonoids", Curr. Opin. Biotechnol., 2001, pp. 155-160, vol. 12, No. 2.
Hiroyuki Kuwahara et al., "Temperature Control of Fimbriation Circuit Switch in Uropathogenic *Escherichia coli* Quantitative Analysis via Automated Model Abstraction", Computational Biology, Mar. 2010, pp. 1-22, vol. 6, No. 3.
James M. Clomburg et al., "Anaerobic fermentation of glycerol: a platform for renewable fuels and chemicals", Trends in Biotechnology, Jan. 2013, pp. 20-28, vol. 31, No. 1.
Jeremy H. Toyn et al., "A counterselection for the tryptophan pathway in yeast: 5-fluoroanthranilic acid resistance", Yeast, 2000, pp. 553-560, vol. 16.
Jin Y. Yen, "Finding the K Shortest Loopless Paths in a Network", Management Science, Jul. 1971, pp. 712-716, vol. 17, No. 11.
Jose L. Avalos et al., "Compailmentalization of metabolic pathways in yeast mitochondria improves the production of branched-chain alcohols", Nature Biotechnology, Apr. 2013, pp. 335-341, vol. 31, No. 4.
Karoline Faust et al., "Metabolic Pathfinding Using RPAIR Annotation", J. Mol. Biol., 2009, pp. 390-414, vol. 388.

Kengo Ida et al., "Eliminating the isoleucine biosynthetic pathway to reduce competitive carbon outflow during isobutanol production by *Saccharomyces cerevisiae*", Microbial Cell Factories, 2015, pp. 1-9, vol. 14, No. 62.
Kent McClymont et al., "Metabolic tinker: an online tool for guiding the design of synthetic metabolic pathways", Nucleic Acids Research, 2013, pp. 1-9, vol. 41, No. 11.
Kevin V. Solomon et al., "Tuning Primary Metabolism for Heterologous Pathway Productivity", ACS Synthetic Biology, 2013, pp. 126-135, vol. 2.
Kristala L. Jones Prather et al., "De novo biosynthetic pathways: rational design of microbial chemical factories", ScienceDirect, Current Opinion in Biotechnology, 2008, pp. 468-474, vol. 19.
M.L. Green et al., "Genome annotation errors in pathway databases due to semantic ambiguity in partial EC numbers", Nucleic Acids Research, 2005, pp. 4035-4039, vol. 33, No. 13.
Meric Ataman et al., "Heading in the right direction: thermodynamics-based network analysis and pathway engineering", ScienceDirect, Current Opinion in Biotechnology, 2015, pp. 176-182, vol. 36.
Miguel A. Campodonico et al., "Generation of an atlas for commodity chemical production in *Escherichia coli* and a novel pathway prediction algorithm, GEM-Path", Metabolic Engineering, 2014, pp. 140-158, vol. 25.
Minoru Kanehisa et al., "Data, information, knowledge and principle: back to metabolism in KEGG", Nucleic Acids Research, 2014, pp. D199-D205, vol. 42.
Monica Cavia-Siaz et al., "Antioxidant properties, radical scavenging activity and biomolecule protection capacity of flavonoid naringenin and its glycoside naringin: a comparative study", J. Sci. Food Agric., 2010, pp. 1238-1244, vol. 90.
Pablo Carbonell et al., "XTMAS: pathway design in an eXTended metabolic space", Nucleic Acids Research, 2014, pp. W389-W394, vol. 42.
Patrick C. Cirino et al., "Engineering *Escherichia coli* for Xylitol Production From Glucose-Xylose Mixtures", InterScience, Biotechnology and Bioengineering, Dec. 20, 2006, pp. 1167-1176, vol. 95, No. 6.
Pietro Alifano et al., "Histidine Biosynthetic Pathway and Genes: Structure, Regulation, and Evolution", Microbiological Reviews, Mar. 1996, pp. 44-69, vol. 60, No. 1.
Priti Pharkya et al., "OptStrain: A computational framework for redesign of microbial production systems", Genome Research, 2004, pp. 2367-2376, vol. 14.
S.A. Rahman et al., "Metabolic pathway analysis web service (Pathway Hunter Tool at CUBIC)", Bioinformatics, 2005, pp. 1189-1193, vol. 21, No. 7.
Syed Shams Yazdani et al., "Anaerobic fermentation of glycerol: a path to economic viability for the biofuels ndustry", Current Opinion in Biotechnology, 2007, pp. 213-219, vol. 18.
Tadas Jakociunas et al., "CRISPR/Cas9 advances engineering of microbial cell factories", Metabolic Engineering, 2016, pp. 44-59, vol. 34.
Vassily Haizimanikatis et al., "Exploring the diversity of complex metabolic networks", Bioinformatics, 2005, pp. 1603-1609, vol. 21, No. 8.
Xueming Tang et al., "Microbial Conversion of Glycerol to 1,3-Propanediol by an Engineered Strain of *Escherichia coli*", Applied and Environmental Microbiology, Mar. 2009, pp. 1628-1634, vol. 75, No. 6.
Yaakov Nahmias et al., "Apolipoprotein B-Dependent Hepatitis C Virus Secretion Is Inhibited by the Grapefruit Flavonoid Naringenin", Hepatology, Mar. 2008, pp. 1437-1445, vol. 47, No. 5.
Yan-Zhen Mei et al., "Biocatalysis and biotransformation of resveratrol in microorganisms", Biotechnol. Lett., 2015, pp. 9-18, vol. 37.
Yugo Shimizu et al., "Generalized Reaction Patterns for Prediction of Unknown Enzymatic Reactions", Genome Inform., 2008, pp. 149-158.
Yuki Moriya et al., "PathPred: an enzyme-catalyzed metabolic pathway prediction server", Nucleic Acids Research, 2010, pp. W138-W143, vol. 38.
Yunzi Luo et al., "Engineered Biosynthesis of Natural Products in Heterologous Hosts", Chem. Soc. Rev., Aug. 2015, pp. 5265-5290, vol. 44, No. 15.

(56) References Cited

OTHER PUBLICATIONS

Zachary L. Fowler et al., "Biosynthesis and biotechnological production of flavanones: current state and perspectives", Appl. Microbiol. Biotechnol., 2009, pp. 799-808, vol. 83.

Blum, T., et al., "MetaRoute: Fast Search for Relevant Metabolic Routes for Interactive Network Navigation and Visualization," Bioinformatics, Jul. 16, 2008, vol. 24, No. 18, pp. 2108-2109.

Hollman, P.C.H., et al., "Bioavailability and Health Effects of Dietary Flavonols in Man," Archives of Toxicology Supplement, Feb. 1998, vol. 20, pp. 237-248.

International Search Report in related International Application No. PCT/IB2017/050576, dated May 4, 2017.

Kuwahara, H., et al., "MRE: A Web Tool to Suggest Foreign Enzymes for the Biosynthesis Pathway Design with Competing Endogenous Reactions in Mind," Nucleic Acids Research, Apr. 29, 2016, vol. 44, No. W1, pp. W217-W225.

Liberal, R., et al., "PathwayBooster: A Tool to Support the Curation of Metabolic Pathways," BMC Bioinformatics, Mar. 15, 2015, vol. 16, No. 1, BioMed Central.

Pitkänen, E., et al., "Inferring Branching Pathways in Genome-Scale Metabolic Networks," BMC Systems Biology, Oct. 29, 2009, vol. 3, No. 1, Biomed Central Ltd.

Rodrigo, G., et al., "DESHARKY: Automatic Design of Metabolic Pathways for Optimal Cell Growth," Bioinformatics, Nov. 1, 2008, vol. 24, No. 21, pp. 2554-2556.

Written Opinion of the International Searching Authority in related International Application No. PCT/IB2017/050576, dated May 4, 2017.

\* cited by examiner

Host organism (KEGG organism code or name)
(e.g., ECO or Escherichia coli K-12 MG1655)
101 — ECO Starting material (KEGG compound ID or name)
(e.g., C00031 or D-Glucose or Grape sugar)
102 — C00082

Desired product (KEGG compound ID or name)
(e.g., C00022 or Pyruvate or 2-Oxopropanoate)
103 — nar 104
- Naringin
- Narbomycin
- Naringenin
- Sanguinarine
- (2S)-Naringenin
- Chalconaringenin
- 8-Prenylnaringenin
- (-)-(2S)-Naringenin
- Dihydrosanguinarine
- Naringenin chalcone

FIG. 1B

Host organism (KEGG organism code or name)
(e.g., ECO or Escherichia coli K-12 MG1655)
ECO Starting material (KEGG compound ID or name)
(e.g., C00031 or D-Glucose or Grape sugar)
C00082

Desired product (KEGG compound ID or name)
(e.g., C00022 or Pyruvate or 2-Oxopropanoate)
C00509

☑ Advanced options — 105

Maximum number of reactions in each route — 106
8

Max number of biosynthesis routes — 107
50

KEGG RPAIR constraints — 108
☑ Main ☑ Cofac ☑ Trans ☐ Leave ☐ Ligase

Excluded compounds (one KEGG compound ID per line) — 109

Add
Submit

| NUMBER 201 | SCORE 202 | ROUTE 203 | REACTIONS 204 | ECO 205 |
|---|---|---|---|---|
| 1 | -15.03 | C00082 → C00811 → C00223 → C06561 → C00509 | 0:4 | NO |
| 2 | -15.61 | C00082 → C00811 → C00223 → C17743 → C00083 → C06561 → C00509 | 0:6 | NO |
| 3 | -21.04 | C00082 → C00811 → C01197 → C01494 → C00406 → C00223 → C06561 → C00509 | 0:8 | NO |
| 4 | -21.04 | C00082 → C00811 → C01197 → C00323 → C00406 → C17742 → C00223 → C06561 → C00509 | 0:8 | NO |
| 5 | -21.10 | C00082 → C00811 → C00223 → C17742 → C17740 → C00083 → C06561 → C00509 | 0:7 | NO |
| 6 | -21.53 | C00082 → C00811 → C00223 → C17742 → C17740 → C17743 → C00083 → C06561 → C00509 | 0:8 | NO |
| 7 | -22.11 | C00082 → C00811 → C00223 → C17743 → C17740 → C00083 → C06561 → C00509 | 0:7 | NO |
| 8 | -22.11 | C00082 → C00811 → C00223 → C00164 → C00332 → C00083 → C06561 → C00509 | 0:7 | NO |
| 9 | -23.88 | C00082 → C00022 → C00033 → C00164 → C00332 → C00083 → C06561 → C00509 | 3:4 | NO |
| 10 | -23.88 | C00082 → C01179 → C00209 → C00033 → C00332 → C00083 → C06561 → C00509 | 3:5 | NO |

List of the endogenous reactions competing with reaction
Malonyl-CoA:4-Coumaroyl-CoA malonyltransferase(cyclizing)(R01613) for
compound Malonyl-CoA (C00083) in Escherichia coli K-12 MG1655(ECO):

| Reaction | Gibbs Energy | Enzyme Gene ID |
|---|---|---|
| acetyl-CoA:carbon dioxide ligase (ADP-forming) (R00742) | 4.4248 | b0185(accA)<br>b2316(accD)<br>b3256(accC) |
| carboxybiotin-carboxyl-carrier-protein-CoA carboxytranferase (R04386) | not determined | b0185(accA)<br>b2316(accD)<br>b3256(accC) |
| Malonyl-CoA:[acyl-carrier-protein] S-malonyltransferase (R01626) | not determined | b1092(fabD) |

501     FIG. 5     502     503

Pathway Number 1: C00082 (R00737) C00811 (R01616) C00223 (R01613) C06561 (R02446) C00509
Download all potential cDNA gene sequences in fasta format for this pathway

| Reaction ID (Compound ID) | Formula | ECO | Gibbs Energy | EC # | Potential Enzyme | Competing Reaction (Gibbs Energy) |
|---|---|---|---|---|---|---|
| R00737 (C00082) | C00082 ⇌ C00811 + C00014 | No | -38.0617 | 4.3.1.23 | hha:Hhal_1820 and more | R00734 (0.2967) and more |
| R01616 (C00811) | C00002 + C00811 + C00010 ⇌ C00020 + C00013 + C00223 | No | -9.7 | 6.2.1.12 | soc:105193785 and more | None |
| R01613 (C00223) | C00223 + 3 C00083 ⇌ C06561 + 4 C00010 + 3 C00011 | No | 37.1831 | 2.3.1.74 | ath:AT5G13930 (TT4) and more | R00742 (4.4248) and more |
| R02446 (C06561) | C06561 ⇌ C00509 | No | -236.4537 | 5.5.1.6 | ath:AT3G55120 (TT5) and more | None |

FIG. 13

METHOD FOR DETERMINING HETEROLOGOUS BIOSYNTHESIS PATHWAYS

CROSS-REFERENCE TO RELATED APPLICATIONS

This application is the National Stage of International Application No. PCT/IB2017/050576, filed Feb. 2, 2017, which claims the benefit of and priority to U.S. Provisional Patent Application Ser. No. 62/291,308 filed Feb. 4, 2016, which is incorporated herein by reference in its entirety.

TECHNICAL FIELD

The present invention relates to a method and system for analyzing, determining, predicting and displaying ranked suitable heterologous biosynthesis pathways for a specified host.

BACKGROUND OF THE INVENTION

High-value natural products can be constructed through biosynthesis using recent advances in genome editing and metabolic engineering. Known methods and systems for graphically displaying biosynthesis pathways for natural product construction, for the most part, simply provide for the display of a selection of certain data on a graphical user interface. These prior art graphical systems fail to account for essential analytical functionality of host parameters that is needed to accurately calculate biosynthesis pathways in a high speed system with accuracy and enhanced usability.

Many design decisions must be made when analyzing possible biosynthesis pathways for a natural product, but prior art graphical display programs do not adequately account for several key decisions, such as the problems associated with foreign gene introduction into a host organism and the suitability of pathways for the endogenous metabolism of a host organism. Specifically, one design decision that may be made for engineering of heterologous biosynthesis systems concerns the decision of which foreign metabolic genes to introduce into a given host organism. The introduction of foreign metabolic genes into the biosynthesis analysis is a decision that must be made based on multifaceted factors, such as the suitability of pathways for the endogenous metabolism of a host organism, in part because the efficacy of heterologous biosynthesis is affected by competing endogenous pathways.

Known graphical user display systems do not accurately calculate biosynthesis pathways considering this suitability of pathways for the endogenous metabolism of a host organism to maximize speed of the system with accuracy and enhanced usability, which means known systems are not as accurate as possible concerning the design decision of introduction of foreign metabolic genes into a given host organism.

For instance, several known graphical display systems do not allow the user to specify a host organism in the determination of pathways of construction for a natural product using biosynthesis, such as the graphical systems known as BNICE, PredPath and Metabolic tinker, which were developed to explore pathways irrespective of the consideration for host organisms.

TABLE 1a

Graphical Display Systems.

| Tool | Access | Chassis | Chemical transformation | Thermodynamic consideration | Ranking score | Information given for each pathway | (Ref.) |
|---|---|---|---|---|---|---|---|
| BNICE | Closed access | No host | Predicted reactions | No | No pathway ranking | 3-level EC number for each predicted chemical transformation | 7 |
| PathPred | Open access web server | No host | Predicted reactions | No | Chemical similarity | Final compound of biodegradation, predicted intermediates and reactions, confidence for each predicted reaction | 5 |
| Metabolic tinker | Open access web server | No host | RHEA reactions | Directionality, favorability | Net favorability | Possible reactions for each chemical transformation step and net favorability | 4 |

These graphical systems cannot assess the suitability of pathways in a specific context without appropriately considering the introduction foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Several other known graphical display systems do not adequately analyze the basis for the chemical transformation of intermediate precursors that form metabolic routes in a pathway display, such as the FMM, DESHARKY and Metabolic tinker display systems (in Table 1a, above), which specify chemical transformation using metabolic reaction sets from databases. Through the use of metabolic reaction sets from databases, these display systems that do not adequately consider the basis for chemical transformation of intermediate precursors that forms metabolic routes.

TABLE 1b

Graphical Display Systems.

| Tool | Access | Chassis | Chemical transformation | Thermodynamic consideration | Ranking score | Information given for each pathway | (Ref.) |
|------|--------|---------|------------------------|-----------------------------|---------------|-----------------------------------|--------|
| FMM | Open access web server | Many choices | KEGG reactions | No | Number of reaction steps | EC numbers for enzymes, availability of each enzyme in various host organisms, suggestion for foreign enzymes | 1 |
| DESHARKY | Free download | E. coli | KEGG reactions | No | Growth rate | Source or target compound, EC numbers for enzymes, genes for some foreign enzymes, growth rate reduction measures | 6 |

The above display systems do not adequately consider the basis for chemical transformation of intermediate precursors that form metabolic routes, but instead consider only reaction sets from databases. For that reason, these graphical display systems cannot adequately assess the suitability of pathways in a specific context without appropriately considering the introduction foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Other known graphical display systems do not adequately analyze the basis for the chemical transformation of intermediate precursors that form metabolic routes in a pathway display, such as graphical display systems that include BNICE (in Table 1a, above), PredPath (in Table 1a, above) and XTMS, which merely predict some generalized chemical transformation rules using such curated reaction sets and apply those generalized rules to expand potentially feasible metabolic routes.

display, such as Metabolic tinker (in Table 1a, above) and XTMS (in Table 1c, above), which use thermodynamic data to constrain the reaction directionality or to rank pathways based on their net favorability. These systems do not adequately consider competing endogenous reactions; and, therefore, these graphical display systems cannot adequately assess the suitability of pathways in a specific context without appropriately considering the introduction of foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Some graphical display systems allow for the consideration of one specific host organism in the analysis, such as the display systems that restrict the user to consider *Escherichia coli* as a host organism. Graphical display systems that restrict the user to consider *Escherichia coli* as a host organism are based on flux balance analysis (FBA), such as XTMS (in Table 1a, above), DESHARKY (in Table 1a, above), OptStrain and GEM-Path, are specific to the TABLE 1c Graphical Display Systems

| Tool | Access | Chassis | Chemical transformation | Thermodynamic consideration | Ranking score | Information given for each pathway | (Ref.) |
|------|--------|---------|------------------------|-----------------------------|---------------|-----------------------------------|--------|
| XTMS | Open access web server | E. coli | Predicted reactions | Favorability | Gene scores, reaction steps, toxicity, yield, Gibbs energy | Source compound for the retrosynthesis path, predicted reactions with EC numbers, genes for foreign enzymes, toxicity, production yield | 3 |

Because these graphical systems only consider curated reaction sets and use generalized rules to expand on possible routes, these graphical display systems cannot adequately assess the suitability of pathways in a specific context without appropriately considering the introduction foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Other known graphical display systems do not adequately analyze the basis for the chemical transformation of intermediate precursors that form metabolic routes in a pathway

*Escherichia coli* chassis. While FBA-based tools tend to offer certain information to evaluate de novo pathways, these systems demand detailed knowledge of a given metabolic system with tight reaction-flux boundaries in order to identify meaningful steady-state flux distributions among a large number of candidate solutions.

Such detailed data are only available for well-studied organisms, and this may be a major reason why FBA-based tools focus exclusively on the pathway design in *E. coli*. Because these graphical display systems are restricted in the type of host organism to be evaluated, these graphical display systems cannot adequately assess the suitability of pathways in a specific context without appropriately considering the introduction of foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Some other graphical display systems, such as FMM and PHT, allow the user to select a host organism from a large set of choices, but these graphical display systems do not use the chassis information to rank suitable biosynthesis pathways for a given endogenous metabolic system. Instead, the PHT display system just reports and displays which enzymes are not natively available in the host, and the FMM display system suggests the introduction of foreign enzymes for certain reactions in heterologous pathways.

cursors that form metabolic routes in a pathway display, or (3) predict some generalized chemical transformation rules using such curated reaction sets and apply them to expand potentially feasible metabolic routes, or (4) restrict the user to use one specific host organism, use thermodynamic data to constrain the reaction directionality or to rank pathways based on their net favorability, which does not consider competing endogenous reactions, or (5) do not use chasis information to rank suitable biosynthesis pathways for a given endogenous metabolic system.

All of these known graphical display systems cannot adequately assess the suitability of pathways in a specific context without appropriately considering the introduction of foreign metabolic genes into a given host organism or considering the endogenous metabolic system of a host TABLE 1d Graphical Display Systems

| Tool | Access | Chassis | Chemical transformation | Thermodynamic consideration | Ranking score | Information given for each pathway | (Ref.) |
|---|---|---|---|---|---|---|---|
| FMM | Open access web server | Many choices | KEGG reactions | No | Number of reaction steps | EC numbers for enzymes, availability of each enzyme in various host organisms, suggestion for foreign enzymes | 1 |
| PHT | Open access web server | Many choices | KEGG reactions | No | Number of reaction steps | EC numbers for enzymes, local and global compound similarities for each reaction step | 2 |

Because these systems do not use the chassis information to rank suitable biosynthesis pathways for a given endogenous metabolic system, these graphical display systems cannot adequately assess the suitability of pathways in a specific context without appropriately considering the introduction of foreign metabolic genes into a given host organism or considering the endogenous metabolic system of a host organism. Therefore, these prior art graphical display systems fail to account for essential functionality that is needed to accurately calculate suitability of biosynthesis pathways in a high speed system with accuracy and enhanced usability.

Overall, known methods and systems for displaying biosynthesis pathways for natural products, for the most part, simply select and display data for disclosure on a graphical user interface, but these known systems do not accurately or adequately analyze pathways for biosynthesis by properly considering introduction of foreign metabolic genes into a given host organism or the endogenous metabolic system of a host organism. These known prior art display systems: (1) do not specify host organisms at all, or (2) do not analyze the basis for the chemical transformation of intermediate preorganism. For the above reasons, these prior art graphical display systems fail to account for essential functionality that is needed to accurately calculate suitability of biosynthesis pathways in a high speed system with accuracy and enhanced usability.

SUMMARY OF THE INVENTION

The present invention relates to a method and system for analyzing, determining, predicting and displaying ranked suitable heterologous biosynthesis pathways for a specified host. The present invention addresses the problem of finding suitable pathways for the endogenous metabolism of a host organism because the efficacy of heterologous biosynthesis is affected by competing endogenous pathways. The present invention is called MRE (Metabolic Route Explorer), and it was conceived and developed to systematically and dynamically search for, determine, analyze, and display promising heterologous pathways while considering competing endogenous reactions in a given host organism.

TABLE 1e

Feature summary of present invention.

| Tool | Access | Chassis | Chemical transformation | Thermodynamic consideration | Ranking score | Information given for each pathway |
|---|---|---|---|---|---|---|
| MRE | Open access web server | Many choices | Verified KEGG reactions | Boltzmann factor | Fraction of conversions via normalized Boltzmann weights | Required metabolites, EC numbers for enzymes, genes for foreign enzymes, reaction free energy, competing native reactions |

Unlike known prior art display systems, the present invention Metabolic Route Explorer (MRE) disclosed herein focuses on the suggestion of foreign enzymes with well-characterized activities for promising heterologous pathways by taking into account the effects of the existing, endogenous metabolic infrastructure of a host organism. To find promising biosynthesis routes from a large number of potential candidates, thermodynamic data offer useful information. Unlike some other existing pathway display systems, such as Metabolic tinker and XTMS (which use thermodynamic data to constrain the reaction directionality or to rank pathways based on their net favorability, which does not consider competing endogenous reactions), the present invention MRE system uses thermodynamic data to rank pathways in a host-dependent manner from the perspective of the integration of new reactions into the endogenous metabolic system.

In order to suggest actual foreign enzymes for the design of heterologous biosynthesis pathways, the present invention MRE only considers verified reactions as metabolic parts. For each foreign reaction in a suggested heterologous pathway, present invention MRE generates information about endogenous reactions competing for metabolites. Since one effective approach to increase the productivity is to attenuate or eliminate competing reactions, MRE also offers useful insights into how to debottleneck and optimize heterologous pathways.

To rationally design a productive heterologous biosynthesis system, it is essential to consider the suitability of foreign reactions for the specific endogenous metabolic infrastructure of a host. The present invention MRE has been developed, which, for a given pair of starting and desired compounds in a given chassis organism, and dynamically ranks biosynthesis routes from the perspective of the integration of new reactions into the endogenous metabolic system.

The present invention is more than a mere "a mathematical algorithm," "a fundamental economic or longstanding commercial practice," or "a challenge in business." The present invention is a method and system that more accurately, more comprehensively, more systematically and dynamically searches for, determines, analyzes, and displays promising heterologous pathways in the field of natural product construction while considering competing endogenous reactions in a given host organism. The claimed invention has a specific, structured graphical user interface paired with the above prescribed functionality that directly relates to the graphical user interface's structure, which resolves identified problems in the prior art display systems.

For instance, the present invention pairs its graphical user interface with its analysis programming to reduce the time for searching, analysis, and dynamic determination and display of suitable biosynthesis pathways over known prior art display systems, and the present invention achieves more accurate predictions of suitable biosynthesis pathways by adequately assessing the suitability of pathways in a specific context, appropriately considering the introduction foreign metabolic genes into a given host organism, and appropriately considering the endogenous metabolic system of a host organism. The combination of these attributes in the present invention allows researchers to more efficiently and accurately search for, determine, analyze, and display promising heterologous pathways while considering competing endogenous reactions in a given host organism.

The use of an endogenous pathway score (calculated based on one or more of the reaction weights in a given pathway for the reaction, the route from the source compound to the target product, the number of reactions that are native and foreign to the host organism and whether the reactions are endogenous to the host), specific context factors, host organism factors, and endogenous metabolic system factors are inventive concepts in the context of the present system, which allows the present invention to decrease the design cycle time-periods over known display systems by eliminating erroneous, flawed or unsuitable pathways from the display and consideration in the biosynthesis efforts. For the above reasons, the present invention is a graphical display system that properly accounts for essential factors in the biosynthesis analysis to more accurately calculate suitability of biosynthesis pathways in a high speed system with greater accuracy, enhanced usability, and dynamic displays.

BRIEF DESCRIPTION OF THE DRAWINGS

The above, and other objects and advantages of the present invention will be understood upon consideration of the following detailed description taken in conjunction with the accompanying drawings, in which like reference characters refer to like parts throughout, and in which:

FIG. 1A is the present invention Metabolic Route Explorer (MRE) user-interface query input page showing "auto-completion" field of product;

FIG. 1B is the present invention Metabolic Route Explorer (MRE) user-interface query input page displaying fields available with "advanced options" checked;

FIG. 2 is the present invention Metabolic Route Explorer (MRE) user-interface summary page for the top-ranked biosynthesis routes;

FIG. 5 is the present invention Metabolic Route Explorer (MRE) user-interface page showing competing reactions for a specified biosynthesis route;

FIG. 13 is the present invention Metabolic Route Explorer (MRE) user-interface page showing a chart of the reactions for the top-ranked biosynthesis pathway shown in FIG. 12;

Figure 3:
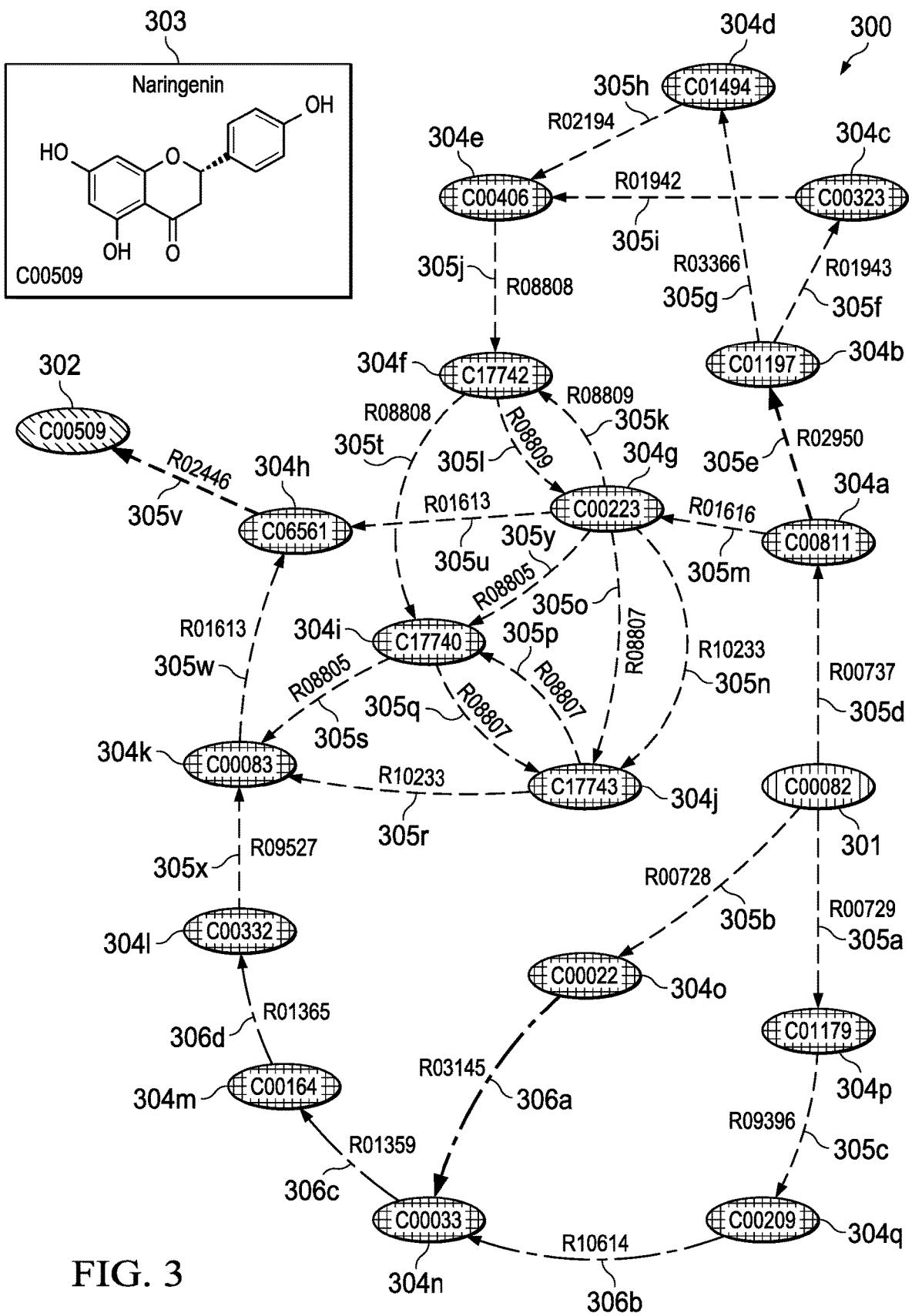
FIG. 3 is the present invention Metabolic Route Explorer (MRE) user-interface page showing a graph of the top-ranked biosynthesis routes.

While the invention is susceptible to various modifications and alternative forms, specific embodiments thereof have been shown by way of example in the drawings and are herein described in detail. It should be understood that the description herein of specific embodiments is not intended to limit the invention to the particular forms disclosed, but on the contrary, the intention is meant to cover all modifications, equivalents, and alternatives falling within the spirit and scope of the invention as defined by the appended claims.

DETAILED DESCRIPTION

The present invention is a method and system of determining heterologous biosynthesis pathways in a specified host, which not only takes into account thermodynamic criteria for the desired reaction, but also considers the effect of competing endogenous reactions and suggests heterologous enzymes that may increase the favorability of the reaction route. Put another way, the present invention relates to a method and system for analyzing, determining, predicting and displaying ranked suitable heterologous biosynthesis pathways for a specified host.

The present invention addresses the problem of finding suitable pathways for the endogenous metabolism of a host organism because the efficacy of heterologous biosynthesis is affected by competing endogenous pathways. The present invention is called MRE (Metabolic Route Explorer), and it was conceived and developed to systematically and dynamically search for, determine, analyze, and display promising heterologous pathways while considering competing endogenous reactions in a given host organism and to suggest possible foreign enzymes that may be suitable for use in the reactions. To rationally design a productive heterologous biosynthesis system, it is essential to consider the suitability of foreign reactions for the specific endogenous metabolic infrastructure of a host. The present invention MRE has been developed, which, for a given pair of starting and desired compounds in a given chassis organism, and dynamically ranks biosynthesis routes from the perspective of the integration of new reactions into the endogenous metabolic system.

To explore biosynthesis routes with MRE, the user specifies a host organism and a pair of the starting and target compounds. To increase its usability and to help the user specify organisms and compounds, MRE comes with an auto-completion feature. With advanced options, the user can override the default setting for the metabolic route search. These options include the maximum number of reaction steps (denoted by n), the number of top-ranked pathways to generate (denoted by K), and a list of compounds that are not considered as primary metabolic precursors in the search, called the exclusion list. By default, n and K are set to 8 and 50, respectively, while the exclusion list has 101 compounds that have high degrees of connectivity in its metabolic network graph, for example, water, ATP and ADP. This exclusion list can also be customized to have other compounds (e.g., $CO_2$). In addition, MRE allows the user to constrain the chemical transformation of precursors based on RPAIR types (e.g., main, cofac and trans). These filtering schemes to constrain possible chemical transformations were reported to increase the relevance of the de novo biosynthesis route suggestion. By default, MRE considers chemical transformations based on main, cofac and trans RPAIR types.

For each promising heterologous biosynthesis pathway, the present invention MRE suggests actual enzymes for foreign metabolic reactions and dynamically generates information on competing endogenous reactions for the consumption of metabolites. These unique, chassis-centered features distinguish the present invention MRE from existing display systems and allow synthetic biologists to dynamically evaluate the design of their biosynthesis systems from a different perspective. As disclosed herein, the present invention MRE (Metabolic Route Explorer) was developed that systematically searches for promising heterologous pathways by considering competing endogenous reactions in a given host organism. The present invention supports biosynthesis of a range of high-value natural products as a case study, and the present inventions MRE has been shown to be an effective tool to guide the design and optimization of heterologous biosynthesis pathways.

The present invention is a novel method and system for determining heterologous biosynthesis pathways to achieve a desired product from a specified host organism considering the suitability of foreign reactions for the specific endogenous metabolic infrastructure of the specified host organism and suggestions of foreign enzymes needed for the reactions using a competition-based weighting approach to determine the top-ranked biosynthesis routes. The present invention has a host-independent metabolic network constructed from databases containing verified metabolic reactions. Weights are assigned to the reactions in host dependent fashion by classifying which enzymatic reactions are native and foreign in the given host organism, by using thermodynamic data, and by identifying competing endogenous reactions. The host-independent metabolic network and weight data are used to construct a metabolic network with host-dependent weights.

The present invention is dynamic and versatile in that it allows user input to select a host organism, source and target compounds, and search options. The present invention Metabolic Route Explorer exhaustively explores and ranks biosynthesis routes for the selected criteria. The present invention MRE generates ranked biosynthesis routes, genes for foreign enzymes and competing native reactions. The results are displayed in summary tables and reaction pathway graphs with links to more detailed graphs and tables with more specific reaction details including reaction formulas, native and foreign enzymes and competing native reactions.

The present invention is a computer program based method and system for determining heterologous biosynthesis pathways to produce a target product in a host organism from a selected starting material. The method and system are characterized as follows:

a. First, a user inputs data, including a host organism, a starting compound, and a desired product. A user may also select other criteria such as the number of reactions per route or the number of routes, the Kyoto Encyclopedia of Genes and Genomes (KEGG™, wherein this term is used in this document from now on as "KEGG," for simplicity) RPAIR constraints, or additional compounds to exclude in the search.

b. Second, a summary of pathways is generated by the Metabolic Route Explorer that ranks the pathways by score, and displays the pathway score summing all of the reaction weights in a given pathway for the reaction, the route from the source compound to the target product, the number of reactions that are native and foreign to the host organism and whether the reactions are endogenous to the host.

c. Next, a graph is generated consisting of the top ten or top thirty routes from the starting compound to the target product, in which vertices represent metabolites and edges represent chemical transformations via verified metabolic reactions.
  i. Color coding of vertices and edges indicate starting and ending compounds, and which reactions are native or foreign to the host organism, and the width of the arrows (edges) indicate the value of the Gibbs energy, or strength, of the reaction path.
  ii. Hovering a cursor over nodes or edges will dynamically display compound names or the reaction Gibbs energy, respectively.

d. From the summary table, a specific route may also be selected and a graph is generated showing the specified route which indicates the pathway from starting compound to target product.
  i. The graph shows the reactions steps and metabolites, as well as competing endogenous reactions.
  ii. With this graph a table of the specific reaction steps for the route is displayed with the reaction identification, reaction formula, whether the reaction is native to the host, the Gibbs energy of the reaction step, the native enzymes, potential foreign enzymes and data for the competing endogenous reactions.
  iii. From this page, a competing reaction can be selected and specific pathway details will be displayed. Selecting an enzymes from the table will generate a display of enzyme data.

The present invention is more than a mere "a mathematical algorithm," "a fundamental economic or longstanding commercial practice," or "a challenge in business." Utilizing the data supplied in the tables and graphs allows a user to select the best path for a specified chemical transformation which is inclusive of thermodynamic criteria for the foreign reaction in view of competing native reactions, and MRE suggests foreign enzymes that may be used to catalyze the desired foreign reactions to increase the desired end product.

The present invention is a method and system that more accurately, more comprehensively, more systematically and dynamically searches for, determines, analyzes, and displays promising heterologous pathways in the field of natural product construction while considering competing endogenous reactions in a given host organism. The claimed invention has a specific, structured graphical user interface paired with the above prescribed functionality that directly related to the graphical user interface's structure, which resolves identified problems in the prior art display systems.

For instance, the present invention pairs its graphical user interface with its analysis programming to reduce the time for searching, analysis, and dynamic determination and display of suitable biosynthesis pathways over known prior are display systems, and the present invention achieves more accurate predictions of suitable biosynthesis pathways by adequately assessing the suitability of pathways in a specific context, appropriately considering the introduction of foreign metabolic genes into a given host organism, and appropriately considering the endogenous metabolic system of a host organism. The combination of these attributes in the present invention allows researchers to more efficiently and accurately search for, determine, analyze, and display promising heterologous pathways while considering competing endogenous reactions in a given host organism.

The use of endogenous pathway score (calculated based on one or more of the reaction weights in a given pathway for the reaction, the route from the source compound to the target product, the number of reactions that are native and foreign to the host organism and whether the reactions are endogenous to the host), specific context factors, host organism factors, and endogenous metabolic system factors are inventive concepts in the context of the present system, which allows the present invention to decrease the design cycle time periods over known display systems by eliminating erroneous, flawed or unsuitable pathways from the display and consideration in the biosynthesis efforts. For the above reasons, the present invention is a graphical display system that properly accounts for essential factors in the biosynthesis analysis to more accurately calculate suitability of biosynthesis pathways in a high speed system with greater accuracy, enhanced usability, and dynamic displays.

FIGS. 1-5 are typical user interface pages of MRE. FIG. 1A is a query input page (100) where a user inputs a host organism, a starting material and a desired product. In the host organism input field (101), a host organism is entered, either by name (e.g. *Escherichia coli* K-12 MG 1655) or by KEGG organism code (e.g. ECO). A starting material is entered in the starting material input field (102) by either KEGG compound ID (e.g. C00031) or name (e.g. D-glucose or grape sugar). The desired product is entered in the desired product input field (103) by either KEGG compound ID (e.g. C00022) or by name (e.g. pyruvate or 2-oxopropanoate). MRE also provides an auto-completion feature. For example, inputting the desired product name generates a drop down list (104) of possible product matches from which the desired product may be selected. When this information is entered, MRE generates a summary page for the top-ranked biosynthesis routes.

FIG. 1B is the query input page (100) with the advanced options feature (105) selected. A user may customize pathway details that will be displayed by specifying ranges in the option fields. The maximum number of reactions in each route (105) can be selected. The default setting for number of reactions is n=8, however, a user can specify up 20 reactions for a route. The maximum number of biosynthesis routes (106), can be selected. The default setting for number of reactions is K=50, however, a user can specify up 500 routes. The KEGG RPAIR (reaction-pair) constraints (108) can be selected. The MRE default setting includes Main, Cofac and Trans, however, a user can remove any of these options or add the Leave or Ligase options. Additional compounds, such as $CO_2$, can be added to the exclusion list in the excluded compounds field (109).

Based on the input query for biosynthesis requirements in FIG. 1, MRE generates the top-K metabolic routes, and the main result page (FIG. 2) summarizes these routes. For each metabolic route, MRE highlights whether it is endogenous or heterologous to the host organism. For each foreign reaction in a heterologous biosynthesis route, MRE predicts which metabolites may not be available in the host, and it lists exogenous genes for the corresponding enzymatic activity and suggests a list of foreign genes based on a taxonomic similarity measure whose cDNA sequences can be downloaded in the FASTA format. It also shows a list of native reactions competing for a metabolic precursor with each foreign enzymatic reaction. MRE provides a means to visualize a specific pathway with competing endogenous reactions as well as a graph aggregating top-ranked routes.

Unlike known prior art display systems, the present invention Metabolic Route Explorer (MRE) disclosed herein focuses on the suggestion of foreign enzymes with well-characterized activities for promising heterologous pathways by taking into account the effects of the existing, endogenous metabolic infrastructure of a host organism. To find promising biosynthesis routes from a large number of potential candidates, thermodynamic data offer useful information. Unlike some other existing pathway display systems, such as Metabolic tinker and XTMS (which use thermodynamic data to constrain the reaction directionality or to rank pathways based on their net favorability, which does not consider competing endogenous reactions), the present invention MRE system uses thermodynamic data to rank pathways in a host-dependent manner from the perspective of the integration of new reactions into the endogenous metabolic system. In order to suggest actual foreign enzymes for the design of heterologous biosynthesis pathways, the present invention MRE only considers verified reactions as metabolic parts. For each foreign reaction in a suggested heterologous pathway, present invention MRE generates information about endogenous reactions competing for metabolites. Since one effective approach to increase the productivity is to attenuate or eliminate competing reactions, MRE also offers useful insights into how to debottleneck and optimize heterologous pathways.

FIG. 2 is an example of a summary page (200) showing a table representation of the ten top-ranked biosynthesis routes for production of naringenin (KEGG compound ID C00509) from L-tyrosine (KEGG compound ID C00082) in an *E. coli* host organism. The summary page will typically display 50 routes (the default setting for K) unless a different number of routes have been selected in the user-input page. In the example table (200), only 10 of the routes are shown. The No. column (201) in the table shows the ranking of the pathway. The Score column (202) shows the score of the pathway wherein the higher the score, the better the route. The score is based on a predetermined calculation, such as, for example, the sum of all reaction weights in a given pathway taking into consideration the thermodynamic criteria of the reactions in the route as well as the effect of endogenous competing reactions.

The Route column (203) shows the steps in the specified metabolic route from the starting material to the target compounds by KEGG compound ID. Alternatively, a user can choose to view the compounds by name instead of ID numbers. The Reactions column (204) shows the number of reactions in the route indicating a ratio of how many of the steps in the pathway are reactions native to the host organism (first number) and how many are foreign reactions for the host organism (second number). Column 205 shows whether the reaction pathway is natively present in the user specified host. The ECO column heading in the example table specifies the host is *E. coli*. "Yes" indicates that the all the reactions exist in the user-specified host and "No" indicates that they do not. In the example table, the reactions listed are not native to the host organism.

FIG. 3 is an example of a graphical representation page (300) of the top-ten ranked biosynthesis routes seen in the FIG. 2 summary page showing the pathway steps for production of naringenin (KEGG compound ID C00509) from L-tyrosine (KEGG compound ID C00082) in an *E. coli* host organism. Alternatively, a user can choose to view a graph of the top 30 routes. The displayed graphs are scalable by the user to allow visualization of graph details.

The example graph shows the L-tyrosine starting compound (301) as an oval with the KEGG compound ID and shows the naringenin desired product (302) as an oval with the KEGG compound ID. Alternatively, a user can choose to view the graph with compound names instead of ID numbers. By hovering over a selected compound, a pop-up box (303) displaying the selected compound by common name, chemical structure and KEGG compound ID can be viewed. In the example, naringenin is displayed in the pop-up box (303). Metabolites are shown by KEGG compound ID in ovals designated 304*a*-304*q* along the reaction pathways.

Reactions in the pathway are shown as arrows or edges in the graph wherein the arrows indicate the direction of the reaction (i.e., the reactants and the products). The width of the arrow indicates the value of the Gibbs energy for the reaction, wherein the stronger the reaction, the wider the arrow will be. In the example, the foreign reaction designated 305*e* has a thicker arrow than the foreign reaction designated 305*d*, indicating that 305*e* is the stronger reaction. Hovering the cursor over a reaction pathway will display the reaction compounds and the reaction's Gibbs energy. Foreign reactions are shown by KEGG reaction IDs along arrows 305*a*-305*y* in the example graph. Native reactions are shown by KEGG reaction IDs along arrows 306*a*-306*d* in the example graph.

A user viewing the page would see the compounds and reaction paths in color, for example, the starting compound (301), the desired product (302) and the metabolites (304*a*-304*q*) would be seen in red, green and yellow, respectively, and the foreign (305*a*-305*y*) and native reaction (306*a*-306*d*) arrows would be seen in cyan and purple, respectively. This allows a user to quickly identify the reaction pathways and whether the pathways are native or foreign to the host organism. For instance, in the example graph, cyan colored arrows (305*a*, 305*b* and 305*d*) would indicate that all three of the reactions beginning with the starting compound (301) are foreign reactions to the *E. coli* host organism.

Figure 4:
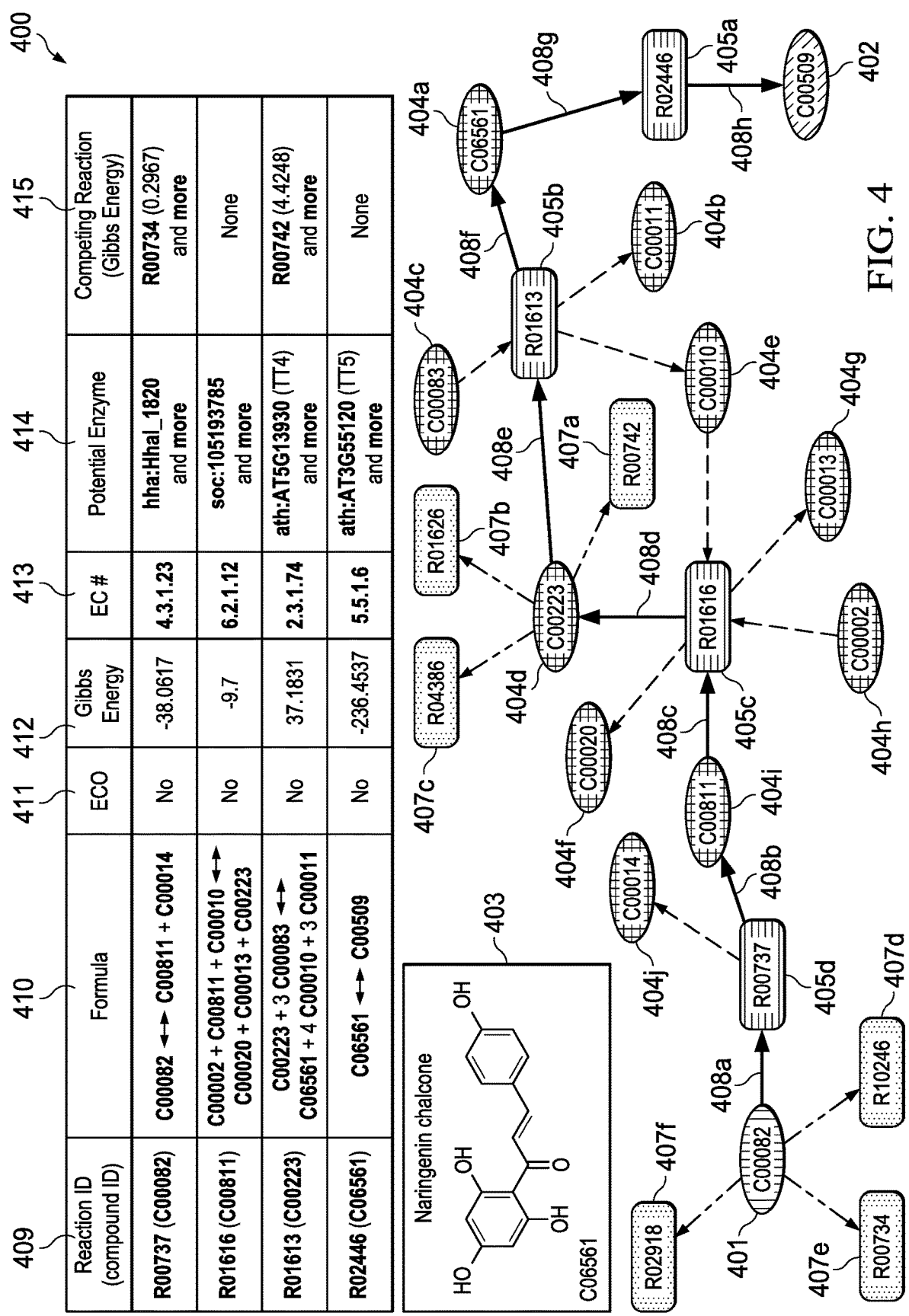
FIG. 4 is the present invention Metabolic Route Explorer (MRE) user-interface page showing a graph of the pathway-level information for a specified biosynthesis route.

FIG. 4 is an example of a pathway-level page (400) showing the graph for only the top-rated biosynthesis route shown on the FIG. 2 summary page for the production of naringenin (KEGG compound ID C00509) from L-tyrosine (KEGG compound ID C00082) in an *E. coli* host organism. This page shows detailed information about each reaction step of a given biosynthesis pathway. This pathway information is displayed in a table and on a graph in this page. This page can be viewed in terms of KEGG IDs or names, and this display choice can be changed with a click on the link shown on top of the page. For each reaction, the table shows the reactants, the products, whether the reaction is endogenous, the standard reaction Gibbs energy, and the corresponding EC number (if it's an enzymatic reaction). If the reaction is based on a heterologous enzyme, a list of potential enzymes and a list of native competing reactions are also shown (with links to more detailed pages) in the table. Moreover, all potential cDNA gene sequences for the pathway are available for download in FASTA format.

The selected reaction pathway from the starting compound (401) to the desired product (402) proceeds along the reaction pathway arrows (408*a*-408*h*) and includes the KEGG reaction IDs for each reaction (405*a*-405*d* and 407*a*-407*f*) and the KEGG compound IDs for compounds that are utilized or produced by the reactions (404*a*-404*j*). The pop-up box (403), which can be viewed by hovering the cursor over a compound, shows the common name, chemical structure and KEGG compound ID for an intermediate compound in the reaction pathway. For this pathway, the reactions seen along route 408*a*-408*h* are foreign reactions (405*a*-405*d*). An important additional piece in information on the detailed graph in FIG. 4 is the inclusion of competing reactions (407a-407f), which can impede the progress of the reaction.

At the top of FIG. 4, the pathway details for the route are broken down in table format. The Reaction ID column (409) displays the KEGG reaction ID for the step as well as the KEGG compound ID for the primary reactant in that step. The Formula column (410) displays the primary reactants and products in the step by KEGG compound ID. Column 411 shows whether the reaction pathway is natively present in the user specified host. The ECO column heading in the example table specifies the host is E. coli. "Yes" indicates that the reaction exists in the user-specified host and "No" indicates that it does not. In the example table, the reactions listed are not native to the host organism. The Gibbs energy column (412) displays the energy associated with the reaction which indicates the favorability of the reaction based on thermodynamic criteria. The EC # column (413) displays the Enzyme Commission number for the enzyme that catalyzes the step and the Potential Enzyme column (414) suggests foreign enzymes that may be utilized in the reaction. The Competing Reaction column (415) displays competing reactions by KEGG reaction ID and Gibbs Energy associated with the competing reaction.

A user viewing the page would see the compounds and reaction paths in color. For example, the desired path is shown with blue arrows (408a-408h). The starting compound (401), the desired product (402) and the metabolites (404a-404j) would be seen in red, green and yellow, respectively, and the foreign (405a-405d) reaction boxes would be seen in cyan. Competing endogenous reactions (407a-407f) are shown as gray boxes. This allows a user to quickly identify the reaction pathways and whether the pathways are native, foreign or competing reaction for the host organism. For instance, in the example graph, gray boxes 407a, 407f would indicate that there are six competing reactions on this route.

Unlike known prior art display systems, the present invention Metabolic Route Explorer (MRE) disclosed herein focuses on the suggestion of foreign enzymes with well-characterized activities for promising heterologous pathways by taking into account the effects of the existing, endogenous metabolic infrastructure of a host organism. To find promising biosynthesis routes from a large number of potential candidates, thermodynamic data offer useful information. Unlike some other existing pathway display systems, such as Metabolic tinker and XTMS (which use thermodynamic data to constrain the reaction directionality or to rank pathways based on their net favorability, which does not consider competing endogenous reactions), the present invention MRE system uses thermodynamic data to rank pathways in a host-dependent manner from the perspective of the integration of new reactions into the endogenous metabolic system. In order to suggest actual foreign enzymes for the design of heterologous biosynthesis pathways, the present invention MRE only considers verified reactions as metabolic parts. For each foreign reaction in a suggested heterologous pathway, present invention MRE generates information about endogenous reactions competing for metabolites. Since one effective approach to increase the productivity is to attenuate or eliminate competing reactions, MRE also offers useful insights into how to debottleneck and optimize heterologous pathways.

FIG. 5 is an example of a competing reaction information page (500) displaying the details for the competing endogenous reactions associated with compound 404d in FIG. 4. Compound 404d is a metabolite in the pathway from reaction 405c to reaction 405b and three endogenous reactions in the host organism (407a, 407b, 407c) are competing with the desired pathway for that compound. The reaction column (501) displays the specifics of the three competing reactions. The Gibbs energy column (502) displays the standard reaction Gibbs energy associated with that competing reaction and the Enzyme gene ID column (503) displays the Enzyme Gene ID for the enzyme in the host organism associated with the competing reaction.

As the display pages represented in FIGS. 1-5 progress, more specific reaction data is provided. FIGS. 1A and 1B are the user input and FIG. 2 shows the top ten routes resulting from that input. FIG. 3 is a graphical representation of the top ten routes displayed in FIG. 2. FIG. 4 is a graphical representation of one selected route from FIG. 3 and provides specific details of the reaction mechanism for that pathway, including any known competing endogenous reactions for each step. The FIG. 5 table displays expanded details of the competing reactions for a given step. MRE also provides self-explanatory pages showing detailed information on compounds, reactions and EC numbers. These pages can be accessed by clicking the internal links on the compound IDs, the reaction IDs and the EC numbers. Moreover, external links to other databases are also provided on these pages as alternatives.

Figure 6:
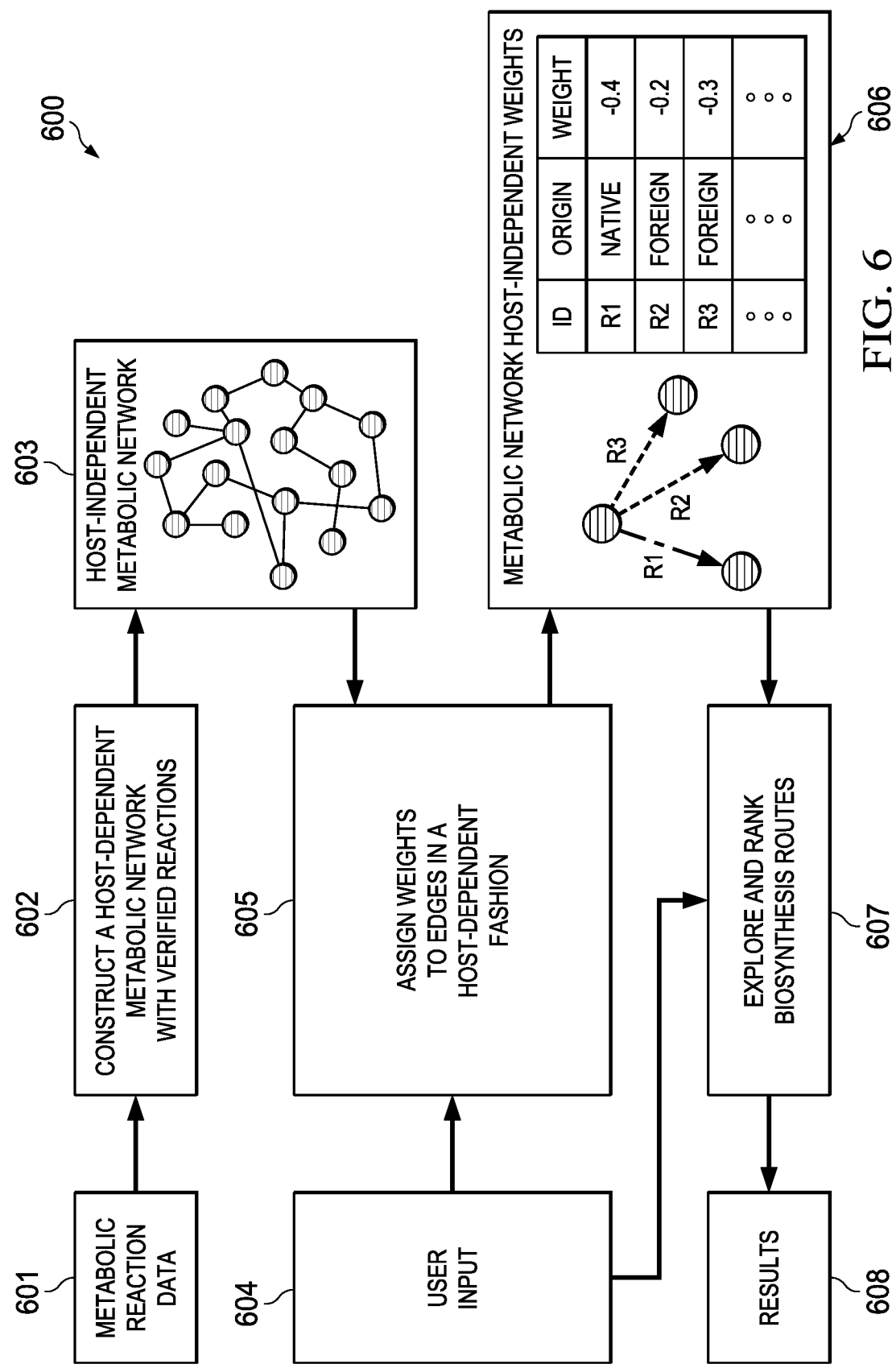
FIG. 6 is the present invention workflow diagram of the Metabolic Route Explorer (MRE)

FIG. 6 depicts the workflow of MRE (600). Metabolic reaction data (601) from several data sources, including but not limited to, the Kyoto Encyclopedia of Genes and Genomes (KEGG), ExPASy ENZYME database, and eQuilibrator dataset are complied. KEGG lists around 4000 organisms, which MRE uses for the selection of a host organism. The KEGG COMPOUND database is used to identify metabolites, while the KEGG REACTION database and the ExPASy ENZYME database are used to find metabolic reactions with verified activities. The eQuilibrator dataset is used to obtain the reaction Gibbs energy in the standard 1M concentration setting. The KEGG RPAIR database is used to restrict search space based on the relation between reactants and products. The KEGG GENES database is used for DNA sequence data for enzymatic genes, and the KEGG taxonomy mapping dataset is used to calculate taxonomic distances.

As seen in FIG. 6, MRE first constructs a directed graph representing a host-independent metabolic network with verified reactions (603). This graph (603) comprises all metabolic reactions with verified activities found in the data source, and it is built regardless of the choice of a host organism for a biosynthesis system. It next assigns weights to the edges in the graph in a host-dependent fashion by classifying which enzymatic reactions are native and foreign in the given host organism and by using the thermodynamic data.

From the metabolic reaction data compiled from the data sources (601), MRE constructs a host-independent metabolic network with verified reactions (602) by first identifying reactions with verified activities. Enzymatic reactions are categorized based on Enzyme Commission numbers (EC numbers). Each EC reaction (i.e., a reaction class corresponding to each EC number) denotes a class of catalytic reactions with the same chemical transformation. To retrieve verified metabolic reactions with known enzymes, reaction classes with partially qualified EC numbers are filtered out as these partial EC reactions are unverified and can lead to misinterpretation of enzymatic activities. EC reactions that do not contain any enzymes are also removed. With this filtering process, 5389 complete EC reactions and 76 spontaneous reactions with verified activities were identified.

Next, standard reaction Gibbs energy $\Delta_r G'^\circ$ is estimated for each of these verified reactions using eQuilibrator with absolute temperature set to 298.15K. Each verified EC reaction is then split into two reactions: the forward reaction with the reaction Gibbs energy $\Delta_r G'^\circ$ and the backward reaction with the reaction Gibbs energy $-\Delta_r G'^\circ$. Those EC reactions whose $\Delta_r G'^\circ$ could not be estimated were assigned the largest of the estimated values for both directions. This conservative approach is used to avoid the suggestion of biosynthesis routes containing reactions with no thermodynamic information as much as possible.

Using these reactions, a directed graph of the host-directed metabolic network (603) is built that models the transformation of metabolites where its vertices represent metabolites and its edges represent chemical transformations via verified metabolic reactions. Since this directed graph unifies all metabolic reactions with verified activities in the reaction databases, its structure is independent of the endogenous metabolic system of any host organism.

User input (604), including host organism, source and target compounds and advanced search options, are used in conjunction with the host independent metabolic network (603) to assign weights to edges of the directed graph in a host-dependent fashion (605). To assign the weight of each outgoing edge from a given compound node, the assumption was made that this reaction was in the host organism and computed the probability of converting the precursor via this reaction over the competing native reactions.

By representing the competition for a metabolic precursor with endogenous reactions by a statistical mechanical model, the probability of each reaction with $\Delta_r G'^\circ$ through the Boltzmann distribution was computed. The logarithm of this computed probability was assigned as the weight of this outgoing edge. The data from the user input (604), the host independent metabolic network (603) and the assigned weights leads to a metabolic network with host-dependent weights (606). Use of this type of statistical mechanics modeling in the context of the biosynthesis system design is novel. Given the metabolic network graph with host-dependent weights (606), MRE will explore and rank biosynthesis routes (607) by exhaustively searching for biosynthesis paths from the given starting material to the given product and generating results (608) of the top-K metabolic routes, each of which has at most n reaction steps. The results (608) include the ranked biosynthesis routes, genes for foreign enzymes and competing native reactions.

In this search to explore and rank biosynthesis routes (607), the compounds in the exclusion list are not considered as intermediate precursors of the product. To rank routes, MRE computes their scores by summing all reaction weights in each route and keeps K routes with the highest scores. MRE transforms the metabolic route search problem into a classical computer science problem known as K-shortest loopless path problem and uses an efficient algorithm to solve it. The core part of the search was implemented in C++.

Figure 7:
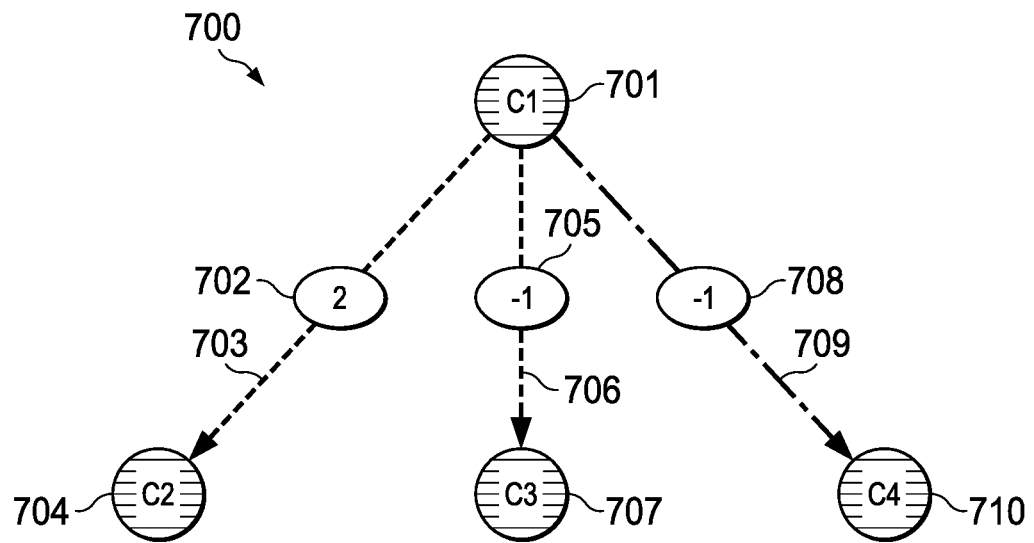
FIG. 7 is the present invention display of an illustration of a thermodynamic favorability-based weighting scheme.
Figure 8:
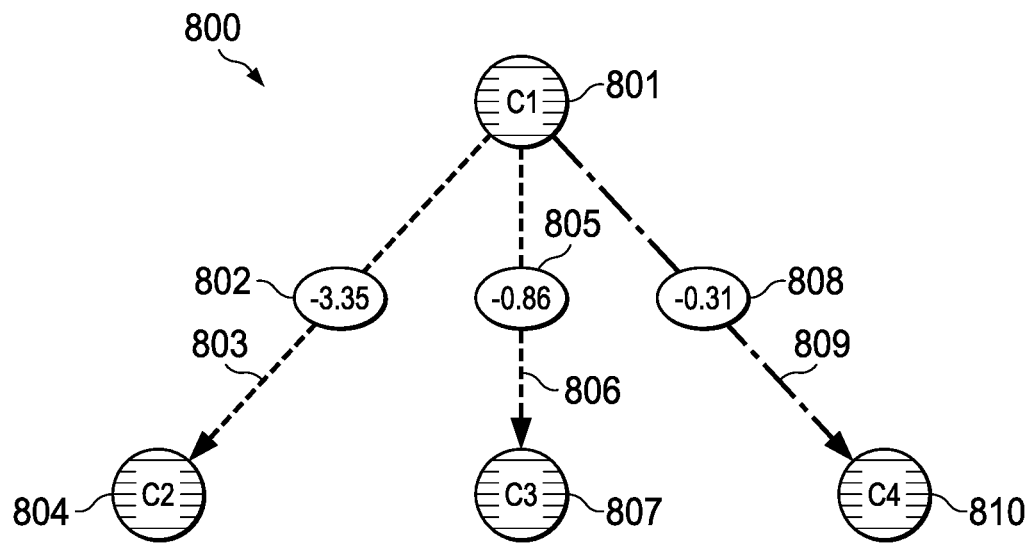
FIG. 8 is the present invention display of an illustration of a competition-based weighting scheme for the same reaction in FIG. 7.

The weighting scheme used to assign weights to edges in a host-dependent fashion (605) depends on a host organism and models the competition for metabolic precursors with the endogenous reactions. Importantly, this competition-based weighting scheme can capture the effects of competing endogenous reactions on heterologous reactions, while a thermodynamic favorability-based weighting scheme cannot. This can make their weight assignments widely different from each other, as illustrated in FIGS. 7 and 8.

To derive a mathematical description of the weighting scheme, a scenario is used to generate weights for edges in the reactions transforming precursor C. Here, RN represents a set of native reactions that can transform C in a given host organism. For each reaction r that can transform C, $e-\Delta\Delta rG'^\circ/RT e-\Delta rG'^\circ/RT$ was set as its Boltzmann factor. Then, f(r), the normalized Boltzmann factor for r, is defined as follows:

$$f(r) = \frac{e^{-\Delta_r G_{ro}/RT}}{1 + e^{-\Delta_r G_{ro}/RT} + \sum_{r' \in R_N \setminus \{r\}} e - \Delta_{r'} G'\circ/RT, f(r)^{e-\Delta rG'\circ/RT}}}$$

(1) where R is the gas constant and T is the absolute temperature. Those reactions that are not in the host organism do not affect the calculation of the Boltzmann distribution. If $r \in RN$, then f(r) is simply based on the Boltzmann distribution of the native reaction system transforming compound C. On the other hand, if $r \notin RN$, then f(r) is based on the Boltzmann distribution of the reaction system that contains all native reactions transforming C and foreign reaction r. With this scheme, every edge in the graph that transforms C in reaction r has the weight log f(r).

FIGS. 7 and 8 demonstrate the differences between a thermodynamic-favorability-based weighting scheme (700) illustrated in FIG. 7 and a competition-based weighting scheme (800) illustrated in FIG. 8.

In the thermodynamic-favorability-based weighting scheme (700) illustrated in FIG. 7, node 701 represents a starting metabolite and nodes 704, 707 and 710 are metabolites from the metabolic conversions via reactions represented by the edges (703, 706 and 709). Edge (arrow) 709 represents a reaction that is native to the host organism and edges 703 and 706 represent foreign reactions. The value within the ovals (702, 706, 708) for each edge represents the weight $\Delta_r G'^\circ/RT$ where R is the gas constant and T is the absolute temperature.

In the competition-based weighting scheme (800) illustrated in FIG. 8, node 801 represents a starting metabolite and nodes 804, 807 and 810 are metabolites from the metabolic conversions via reactions represented by the edges (803, 806 and 809). Edge 809 represents a reaction that is native to the host organism and edges 803 and 806 represent foreign reactions. The value within the ovals (802, 806, 808) for each edge represents its weight. With this scheme, edges (or arrows) with the same $\Delta_r G'^\circ$ value can have different weights in a host-dependent fashion. For example, the weight of C1→C3 is ln [e¹/(1+e¹+e¹)], while that of C1→C4 is ln [e¹/(1+e¹)].

The competition-based weighting scheme illustrated in FIG. 8 is based on the logarithm of normalized Boltzmann weights. Unlike thermodynamic favorability-based measure in FIG. 7, the competition-based weighting scheme estimates a fraction of a given precursor that is converted into next intermediate metabolites. Thus, a pathway score based on the sum of all reaction weights in a given pathway can characterize the lower bound of a fraction of starting material that is converted into the product through this pathway, and the competition-based score can capture the productivity of each pathway more appropriately.

Figure 9:
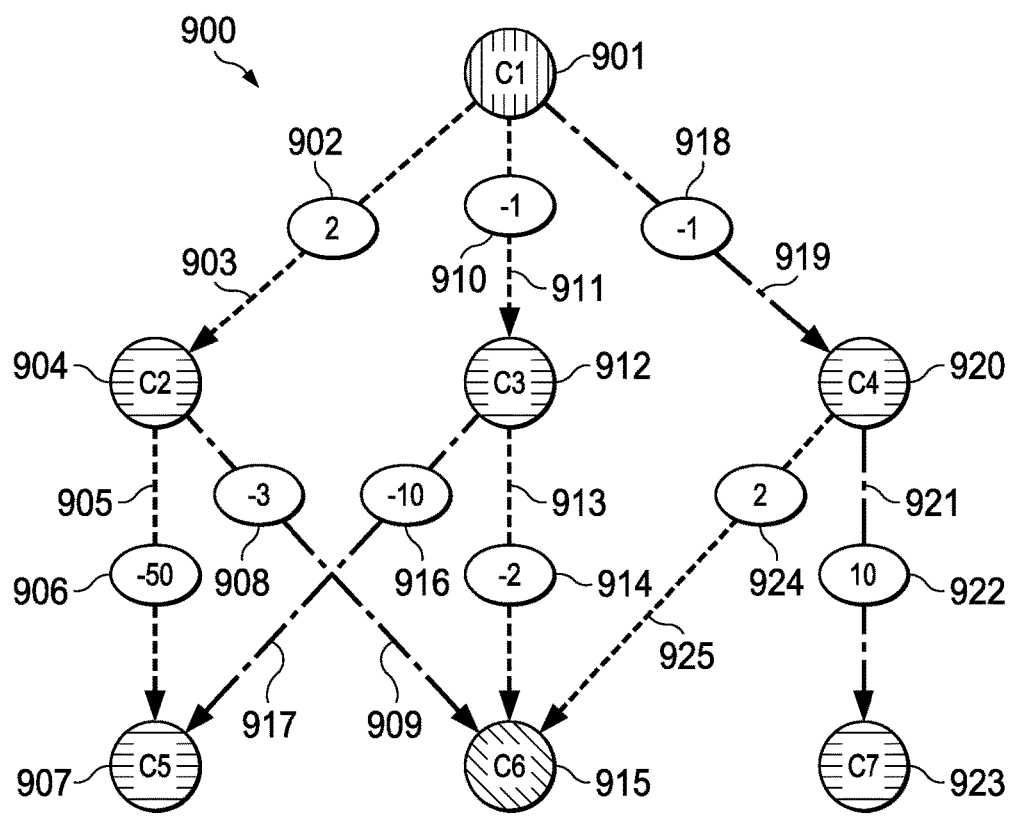
FIG. 9 is the present invention display of a simplified metabolic network showing biosynthesis routes from the C1 starting compound to the C6 product.
Figure 10:
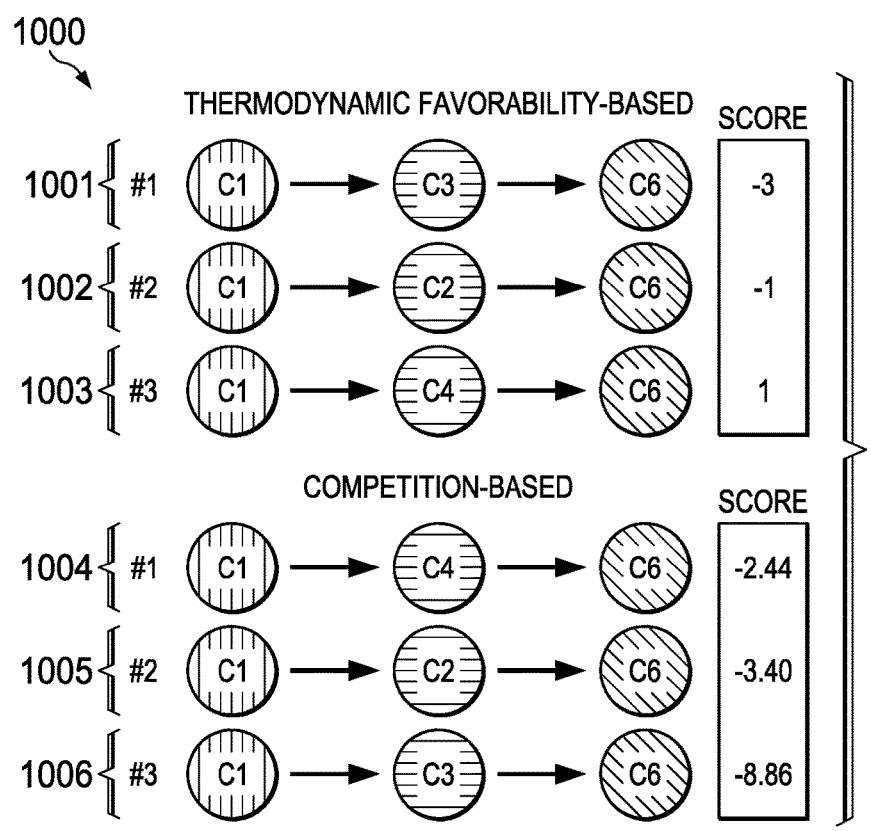
FIG. 10 is the present invention display of an illustration of the difference in ranking outcomes for a thermodynamic favorability-based approach and a competition-based approach.

FIGS. 9 and 10 are an example set showing differences in ranking outcomes between the thermodynamic favorability based approach and utilization of the competition-based approach. FIG. 9 is a simplified metabolic network (900). The nodes (901, 904, 907, 912, 915, 920, 923) are metabolites and the edges (903, 905, 909, 911, 913, 917, 919, 921 and 925) are metabolic conversions. Edges 909, 917, 919 and 921 indicate native reactions, while edges 903, 905, 911, 913 and 925 indicate foreign reactions. The value within the oval for each edge (902, 906, 908, 910, 914, 916, 918, and 922) indicates $\Delta_r G'^\circ/RT$ where R is the gas constant and T is the absolute temperature. In this example, compound C1 (901) is the starting metabolite, and compound C6 (915) is the target product. Three possible routes are shown for the conversion of C1 to C6.

FIG. 10 shows the ranking of the three biosynthesis routes (1000) with the thermodynamic favorability approach (1001, 1002, 1003), wherein the lower the score, the better or more favorable the route, and the competition-based approach (1004, 1005, 1006), wherein the higher the score, the better or more favorable the route. For example, the score of C1→C4→C6 (1003) is $-1+2=1$ with the thermodynamic favorability approach, indicating that the 1003 route is the least favorable of the three routes shown. However, for the competition-based approach the score of C1→C4→C6 (1004) is $\ln[e^1/(1+e^1)]+\ln[e^{-2}/(1+e^{-2}+e^{-10})]$ $=-2.44$ indicating that the 1004 route is the most favorable.

Biosynthesis pathways of interest are often those that transform a higher fraction of a starting material to a target product. One heuristic to rank pathways based on this productivity criterion is the net favorability of pathways. At a first glance, the net thermodynamic favorability (as illustrated in FIGS. 9 and 10) can be seen as a good measure to rank pathways based on this criterion. However, this measure can only quantify the ratio of the target concentration to the source concentration at equilibrium, which may not correspond well with the true picture of the titer of the target product, especially when a given pathway has strong competing reactions and the equilibrium concentration of the starting material is substantially lowered.

Figure 11:
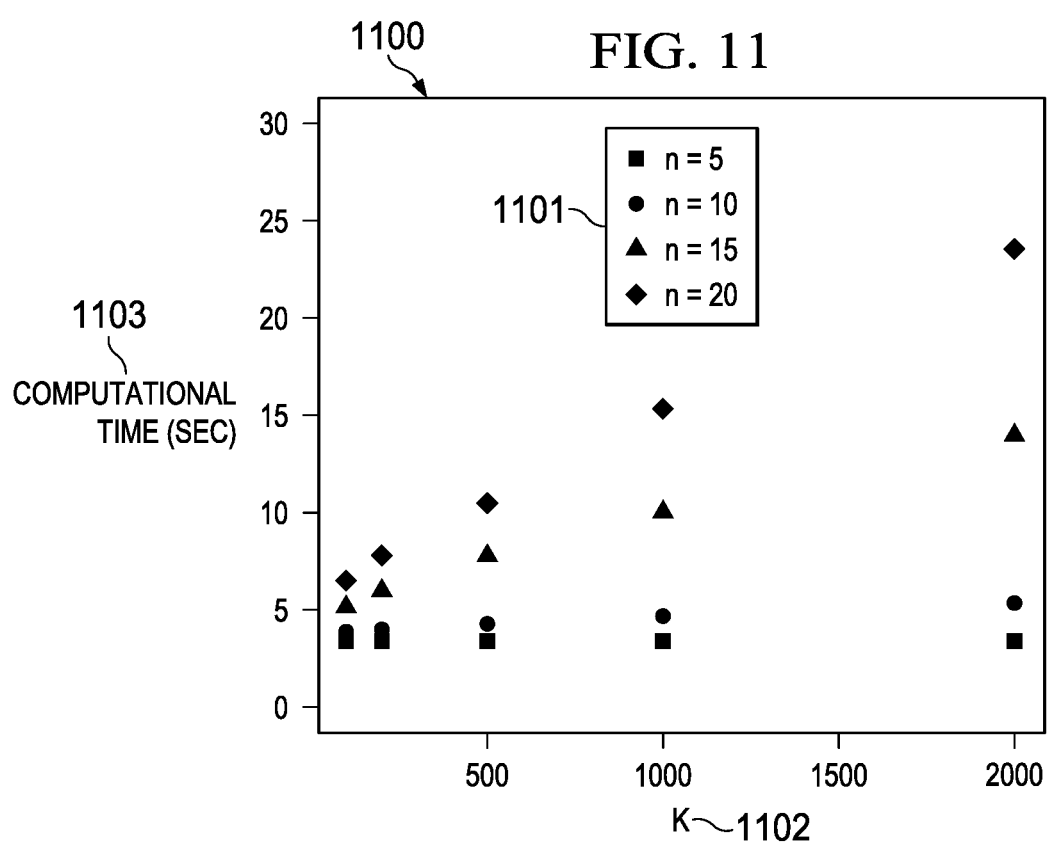
FIG. 11 is the present invention display of a graph demonstrating the computational performance of MRE for various settings.

FIG. 11 is graph showing computational performance of MRE for various settings. On the graph (1100), n (1101) is the maximum number of reaction steps in biosynthesis routes, and K (1102) is the number of top routes that MRE generates. For this analysis, six different pairs of source and target compounds, four settings for the maximum number of reaction steps (n=5, 10, 15 and 20), and five settings for the number of top metabolic routes (K=100, 200, 500, 1000 and 2000) were included. Each point represents the average computational time in seconds (1103) of the six source-target pairs with a given setting for n and K. In this performance test, the default setting of the exclusion list was used. The computation was performed on an Intel Xeon E5-2680 workstation with 256 GB of memory. The computational time increased as the value of n and K increases, but the magnitude of an increase was found to be reasonable. Even with a very computationally demanding setting (i.e. n=20 and K=2000), MRE was able to process the queries within 25 seconds on average. The data also indicated that, with the default setting (i.e. n=8 and K=50), the processing time is expected to be less than 5 seconds. Also, since MRE caps the value of n and K that the user can set at 20 and 500, respectively, the maximum computational time is expected to be around 10 seconds. These show that the exhaustive search employed in MRE does not compromise the user experience based on its processing time.

To further evaluate the computational performance of MRE, the processing time in the runtime environment was measured. 1000 reachable pairs of source and target compounds were randomly selected. With the setting of the largest reaction step size and the largest number of top-ranked pathways (i.e., n=20 and K=500), it took less than 10 seconds for MRE to exhaustively explore routes and process queries on average. In 95% of the samples, the processing time was less than 20 seconds, and even in the worst case, it was just less than 30 seconds. With the default setting (i.e., n=8 and K=50), the processing time was at most 1.36 seconds. The exhaustive pathway search employed in MRE should not compromise the user experience based on its processing time.

Case Study

As a case study, MRE was applied to search for pathways for various biosynthesis specifications using either *E. coli* K-12 MG1655 or *Saccharomyces cerevisiae* as the host organism. Table 2 summarizes the top-ranked heterologous pathways that MRE discovered. This shows that, in biosynthesis of a range of high-value natural products, MRE was able to identify pathways that are known to be productive. The MRE results were also analyzed by comparing them with results from four open-access web servers that can design heterologous biosynthesis pathways, namely, FMM, Metabolic tinker, PHT and XTMS. To explore biosynthesis pathways with these tools, default configurations were used.

TABLE 2

Top-ranked pathways identified by MRE for various biosynthesis specifications

| Biosynthesis specification | | | Results of top-ranked pathway identified by MRE | | | Comparison with existing tools | |
|---|---|---|---|---|---|---|---|
| Source | Target | Host | Steps | Necessary foreign enzymes | Remark | Found a path[a] | Match with MRE[b] |
| L-tyrosine (C00082) | Naringenin (C00509) | *E. coli* (ECO) | 4 | 4.3.1.23, 6.2.1.12, 2.3.1.74, 5.5.1.6 | Recovered a known route as the top route[1] | FMM, XTMS | FMM |
| glycerol (C00116) | 1,3-PDO (C02457) | *E. coil* (ECO) | 2 | 4.2.1.30, 1.1.1.202 | Recovered a known route as the top route[2] | FMM, PHT | FMM, PHT |
| glycerol (C00116) | R-1,2-PDO (C02912) | Yeast (SCE) | 5 | 4.2.3.3, 1.1.1.79, 1.1.1.77 | Recovered a known route as the top route[3] | MT | MT |
| acetyl-CoA (C00024) | artemisinic acid (C20309) | Yeast (SCE) | 10 | 2.5.1.92, 4.2.3.50, 4.2.3.82, 4.2.3.24, 1.14.13.158 | Recovered a known route, and predicted better ones[4] | none | none |
| L-tyrosine (C00082) | resveratrol (C03582) | *E. coli* (ECO) | 3 | 4.3.1.23, 6.2.1.12, 2.3.1.95 | Recovered a known route as the top route[5] | FMM | FMM |

TABLE 2-continued

Top-ranked pathways identified by MRE for various biosynthesis specifications

| Biosynthesis specification | | | Results of top-ranked pathway identified by MRE | | | Comparison with existing tools | |
|---|---|---|---|---|---|---|---|
| Source | Target | Host | Steps | Necessary foreign enzymes | Remark | Found a path[a] | Match with MRE[b] |
| D-xylose (C00181) | xylitol (C00379) | E. coli (ECO) | 2 | 1.1.1.21, 1.1.1.307 | Recovered two known routes as the top routes[6] | FMM, PHT | FMM, PHT |
| PRPP (C00119) | histidine (C00135) | E. coli (ECO) | 8 | 2.6.1.27 | Predicted better and shorter routes than a known native route[7] | FMM, MT | none |
| chorismate (C00251) | tryptophan (C00078) | yeast (SCE) | 5 | none | Predicted the native route as the best, and found shorter routes[8] | FMM, MT, PHT | FMM |

For each biosynthesis specification, the source and target compounds are specified in KEGG ID, and the host organism is in KEGG organism code. For each pathway, the number of reaction steps and the necessary foreign enzymes (in EC number) are specified. Comparison with FMM, Metabolic tinker (MT), PHT and XTMS is also shown. For each tool, its default setting was used, except for the configuration of a pathway length, which was set to accommodate known pathways. In the Table 2, the notation "a" denotes tools that have identified at least one path for a given biosynthesis specification, and the notation "b" denotes tools whose top-ranked pathway is the same as the top-ranked one from MRE.

Biosynthesis of Naringenin

Naringenin is a plant secondary metabolite, which is reported to have various health benefits, including high antioxidant capacities and significant antiviral effects on the hepatitis C virus. Hollman P. C., Katan M. B. Bioavailability and health effects of dietary flavonols in man. Arch. Toxicol. Suppl. 1998; 20:237-248. Owing to inefficiencies in the production of naringenin from natural plant sources, metabolic engineering to have an efficient microbial synthesis of this high-value natural product is thought to be a commercially viable alternative.

Figure 12:
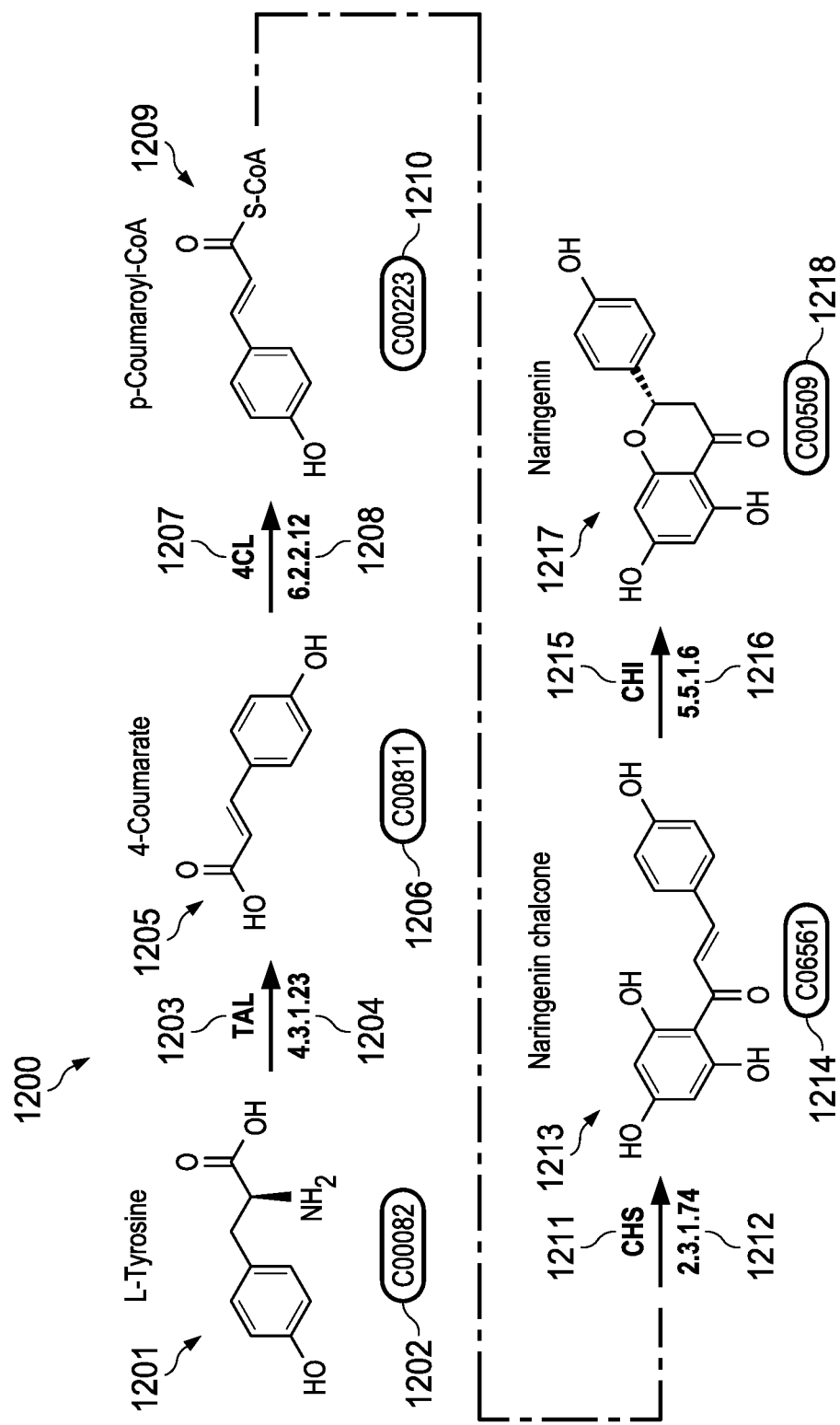
FIG. 12 is the present invention display of the structure of an experimentally derived heterologous biosynthetic pathway for producing naringenin from L-tyrosine in an *E. coli* host.

FIGS. 12 and 13 show a heterologous biosynthesis pathway to produce naringenin from L-tyrosine in an E. coli host. In the analysis seen in FIGS. 12 and 13, L-tyrosine (KEGG compound ID: C00082), an aromatic non-essential amino acid, was selected as the starting material since a state-of-the-art heterologous naringenin production from L-tyrosine in an E. coli strain is known (see FIG. 12). This heterologous biosynthesis route comprises four foreign enzymatic reactions. To analyze the performance of MRE in comparison with other tools, two open-access biosynthesis pathway web servers were applied, Metabolic tinker and XTMS. Since these two recently developed tools also rely on reaction thermodynamic data for their pathway ranking, it was possible to also analyze the effects on the competition-based ranking scheme.

Given this biosynthesis requirement, Metabolic tinker and PHT were not able to find any pathways, while XTMS generated a predicted pathway with hypothetical reactions as its top-ranked candidate. In contrast, the top-ranked route from MRE and FMM was identical to the state of the art. The pathway information given by MRE indicates that the third reaction in the pathway, which transforms p-coumaroyl-CoA into naringenin chalcone, is a bottleneck and competes for the availability of cofactor malonyl-CoA with a more favorable native reaction involved in the fatty acid biosynthesis in the E. coli host (FIG. 13). This suggests that an increase in the concentration of malonyl-CoA or the inhibition of the fatty acid biosynthesis could enhance the productivity of this naringenin biosynthesis pathway. Indeed, previous studies demonstrated that both an increase in the availability of malonyl-CoA in the host and a decrease in the activities in the fatty acid pathway can increase the naringenin titers. While FMM was also able to identify the heterologous naringenin biosynthesis pathway that MRE found, the pathway information given by FMM was not helpful to find an optimization target as FMM does not have a feature to quantify the effects of competing reactions in the host.

FIG. 12 shows the structure of an experimentally derived biosynthesis pathway (1200) from the L-tyrosine starting compound (1201) through the intermediate metabolites (1205, 1209, 1213) to the desired naringenin product (1217). The KEGG compound ID of each metabolite appears in an oval (1202, 1206, 1210, 1214, 1218) below each structure. The required enzyme for each step is noted above the arrows (1203, 1207, 1211, 1215). The abbreviations for the enzymes are: tyrosine ammonia lyase (TAL); 4-coumarate: CoA ligase (4CL); chalcone synthase (CHS) and chalcone isomerase (CHI). The EC numbers (1204, 1208, 1212, 1216) for each reaction are indicated below each arrow.

FIG. 13 displays the information of the top-ranked biosynthesis pathway in MRE for the L-tyrosine to naringenin conversion (which is the same pathway associated with FIG. 4). Column 1301 displays the KEGG reaction and compound IDs. Column 1302 displays the reaction step by KEGG compounds ID. The ECO column (1303) heading in the example table specifies the host is E. coli. "Yes" indicates that the reaction exists in the user-specified host and "No" indicates that it does not. In the example table, the reactions listed are not native to the host organism. Column 1304 displays Gibbs energy. Column 1305 displays EC number for the enzyme if it is an enzymatic reaction. Column 1306 displays potential enzymes that may be used for the reaction and Column 1307 displays competing reactions by KEGG ID and Gibbs energy for the competing reaction.

Production of Value-Added Chemicals from Glycerol

Glycerol is a readily available and relatively inexpensive chemical compound that can be generated in large amounts as a byproduct of biodiesel and bioethanol production processes. Because of its economic viability and long-term sustainability, fermentative production of high-value materials from glycerol has gained much attention recently. Using glycerol as the starting material, pathways were searched for the production of two value-added chemicals, 1,3-propanediol (1,3-PDO), a commodity chemical mainly used to make polyester fiber, and 1,2-propanediol (1,2-PDO), another high-demand commodity chemical used to make a wide range of products including antifreeze, thermoset plastics and cosmetics.

Figure 14:
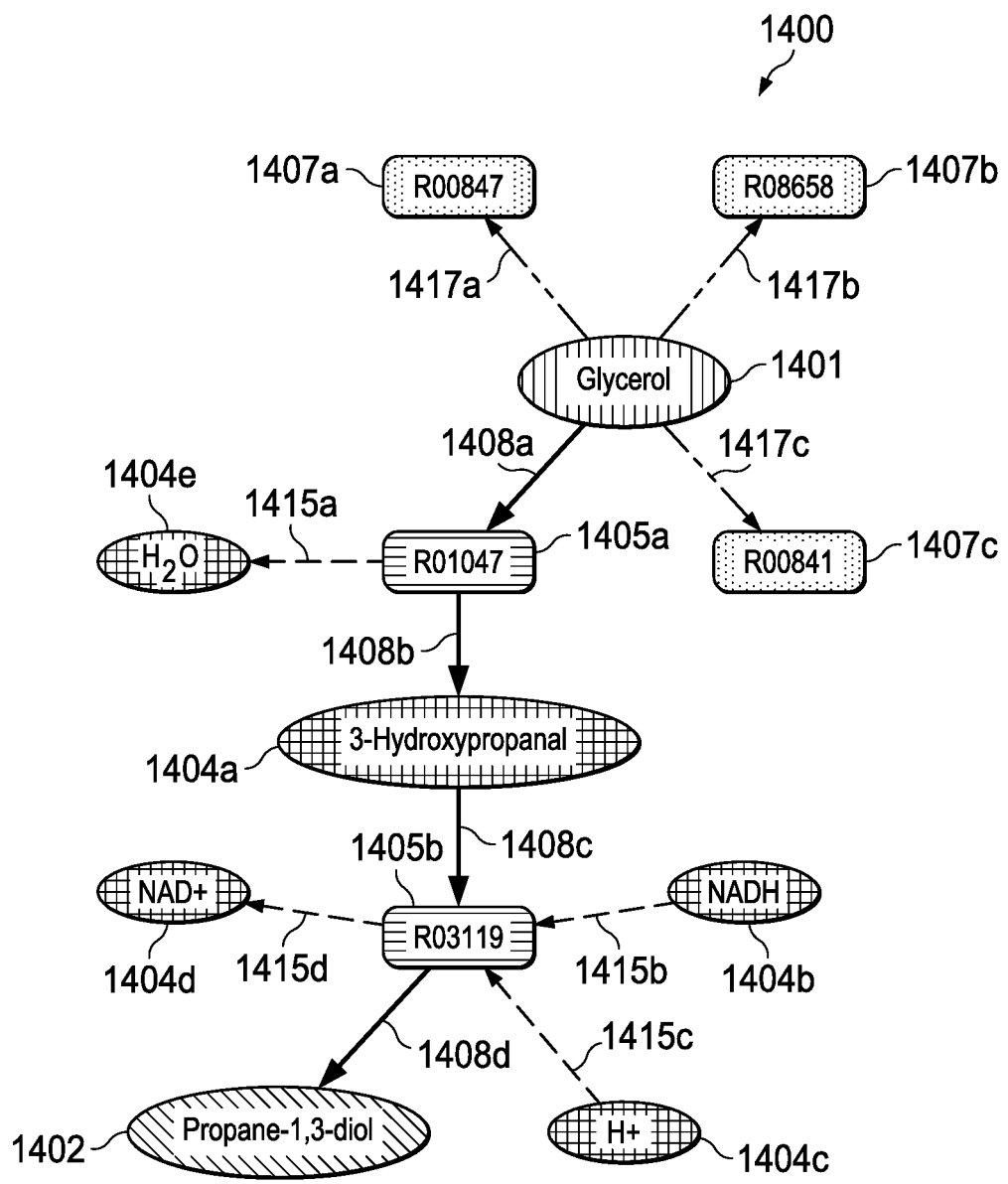
FIG. 14 is the present invention display of a pathway-level graph generated in MRE of the top-ranked pathway for the production of 1,3-PDO from glycerol in *E. coli*.
Figure 15:
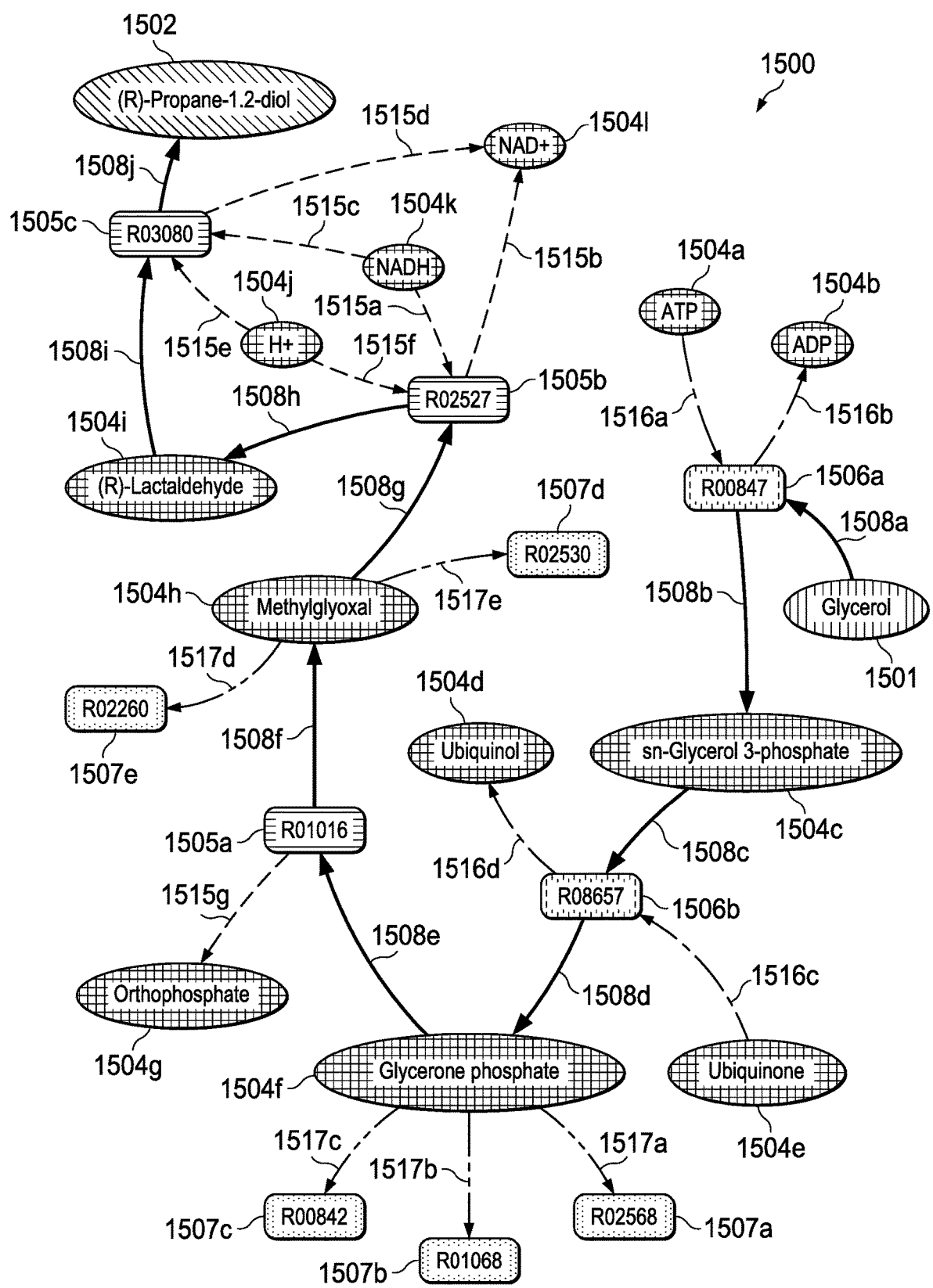
FIG. 15 is the present invention display of a pathway-level graph generated in MRE of the top-ranked pathway for the production of 1,3-PDO from glycerol in yeast.

FIGS. 14 and 15 are pathway level graphs generated in MRE for production of 1,3-propanediol (1,3-PDO) from glycerol in two different host organisms. FIG. 14 shows the MRE top-ranked pathway for the production of 1,3-PDO from glycerol in *E. coli* and FIG. 15 shows the MRE top-ranked pathway for the production of R-1,2-PDO from glycerol in yeast.

MRE was first applied to search for pathways for the production of 1,3-PDO in *E. coli* chassis. The top-ranked pathway (FIG. 14) that MRE identified is a known two-step heterologous pathway, which requires the introduction of a glycerol dehydratase gene and a 1,3-propanediol dehydrogenase gene in the host. Since the first glycerol dehydratase reaction competes for the utilization of glycerol against several native reactions including glycerol kinase, MRE predicts that this can be a target for productivity optimization. Metabolic tinker and XTMS were not able to find any pathways for the 1,3-PDO production, whereas FMM and PHT found the same pathway that MRE identified.

In FIG. 14, the glycerol starting material (1401) is converted to the end product 1,3-PDO (1402) by heterologous reactions 1405a and 1405b, which are foreign to the *E. coli* host, via the reaction route shown by 1408a-1408d. Intermediate metabolites produced or used by these reactions are shown by 1404a-1404e. There are three competing endogenous reactions (1407a, 1407b, 1407c) shown along the arrows (1417a, 1417b, 1417c) which indicate that these reactions, which are native to the *E. coli* host, are competing with reaction 1405a along path 1408a for the glycerol starting product (1401) and foreign reaction pathways are indicated by 1415a-d. In an MRE generated pathway level graph, the display would show starting, ending and intermediate compounds shown in red, green and yellow, respectively. The top-ranked route is shown in blue, while native, foreign and competing reactions and paths are shown in purple, cyan and gray. The color display of pathways and compounds would allow a user to quickly identify the components in each route.

Next, MRE was applied to search for pathways for the synthesis of R-1,2-PDO in the yeast chassis. The top-ranked pathway (FIG. 15) found was a known synthesis pathway for 1,2-PDO. In this pathway, glycerol is first converted to dihydroxyacetone phosphate (DHAP) via two native enzymatic reactions. Methylglyoxal synthase then transforms DHAP into methylglyoxal, which is, in turn, converted into (R)-lactaldehyde. Finally, lactaldehyde reductase is used to produce R-1,2-PDO from (R)-lactaldehyde. FMM and PHT were not able to find any pathways that convert glycerol into R-1,2-PDO, whereas Metabolic tinker identified the same pathway that MRE found as the top-ranked one. Since XTMS focuses on the *E. coli* chassis, this tool was applied to search for heterologous R-1,2-PDO production pathways in *E. coli*; however, no pathways were found.

In FIG. 15, the glycerol starting material (1501) is converted to the end product R 1,2-PDO (1502) by native reactions 1506a and 1506b, which are endogenous to the yeast host and by heterologous reactions 1505a, 1505b and 1505c, which are foreign to the yeast host, via the reaction route shown by 1508a-1508j. Intermediate metabolites produced or used by these reactions are shown by 1504a-1504l. There are five competing endogenous reactions, three (1507a, 1507b, 1507c) are shown along arrows (1517a, 1517b, 1517c) as competing with the desired route for metabolite 1504f, and two reactions (1507d, 1507e) are shown along arrows (1517d, 1517e) as competing with the desired route metabolite 1504h and foreign reaction pathways are indicated by 1515a-f and 1516a-d, respectively. In an MRE generated pathway level graph, starting, ending and intermediate compounds are shown in red, green and yellow, respectively, the top-ranked route is shown in blue, and native, foreign and competing reactions and paths are shown in purple, cyan and gray, which allow a user to quickly identify by color the components in each route.

Production of Artemisinic Acid

Artemisinic acid is an intermediate precursor for antimalaria drug artemisinin, and its production is often celebrated as one of the early success stories of the combination of metabolic engineering and synthetic biology. This engineered biosynthesis pathway utilizes the endogenous mevalonate pathway in budding yeast to transform acetyl-CoA into farnesyl pyrophosphate (FPP), which is then converted into artemisinic acid with heterologous amorphadiene synthase and three-step oxidation reactions.

Figure 16:
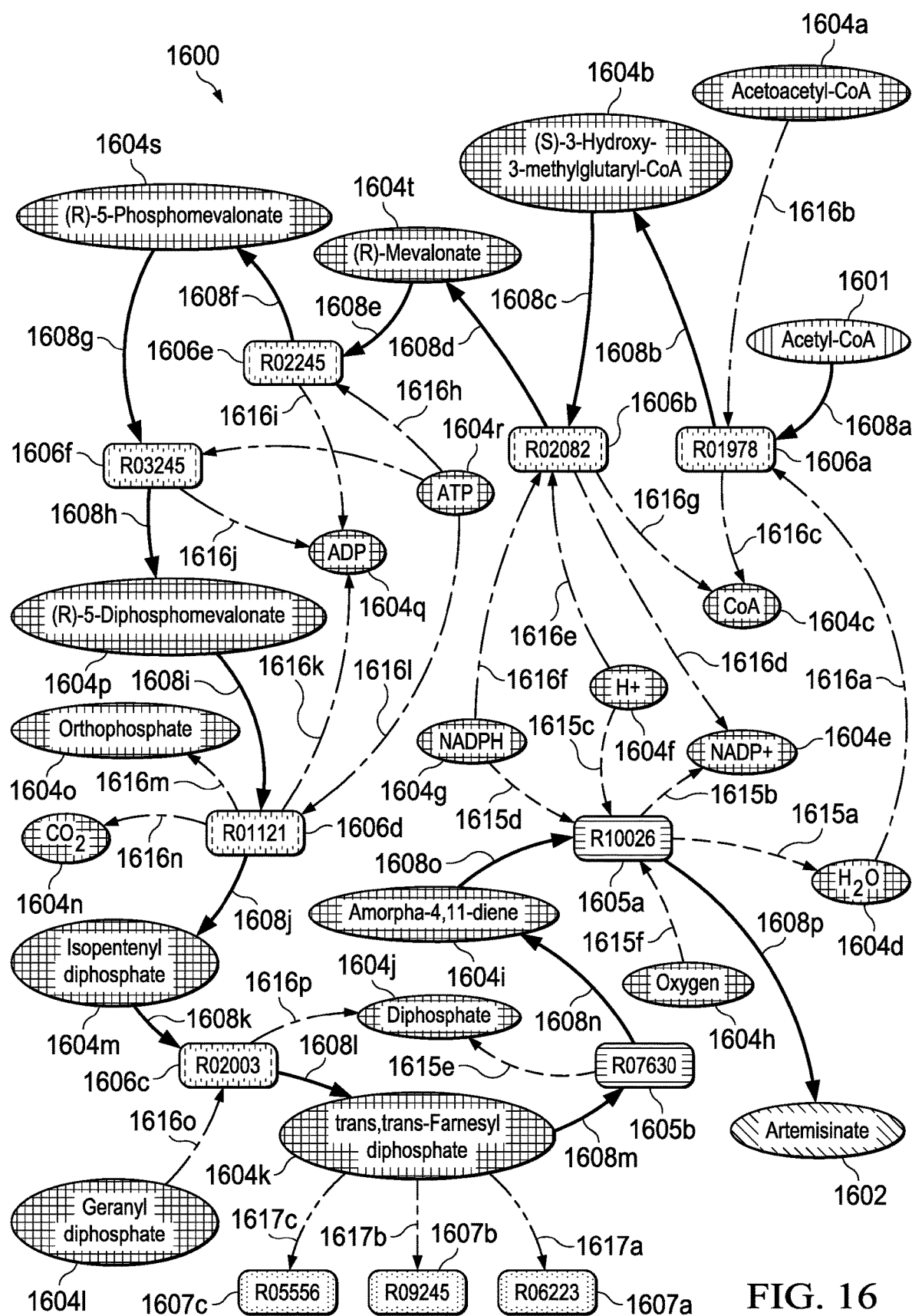
FIG. 16 is the present invention display of a pathway-level graph generated in MRE of a known route for the production of artemisinic acid from acetyl-CoA in yeast.
Figure 17:
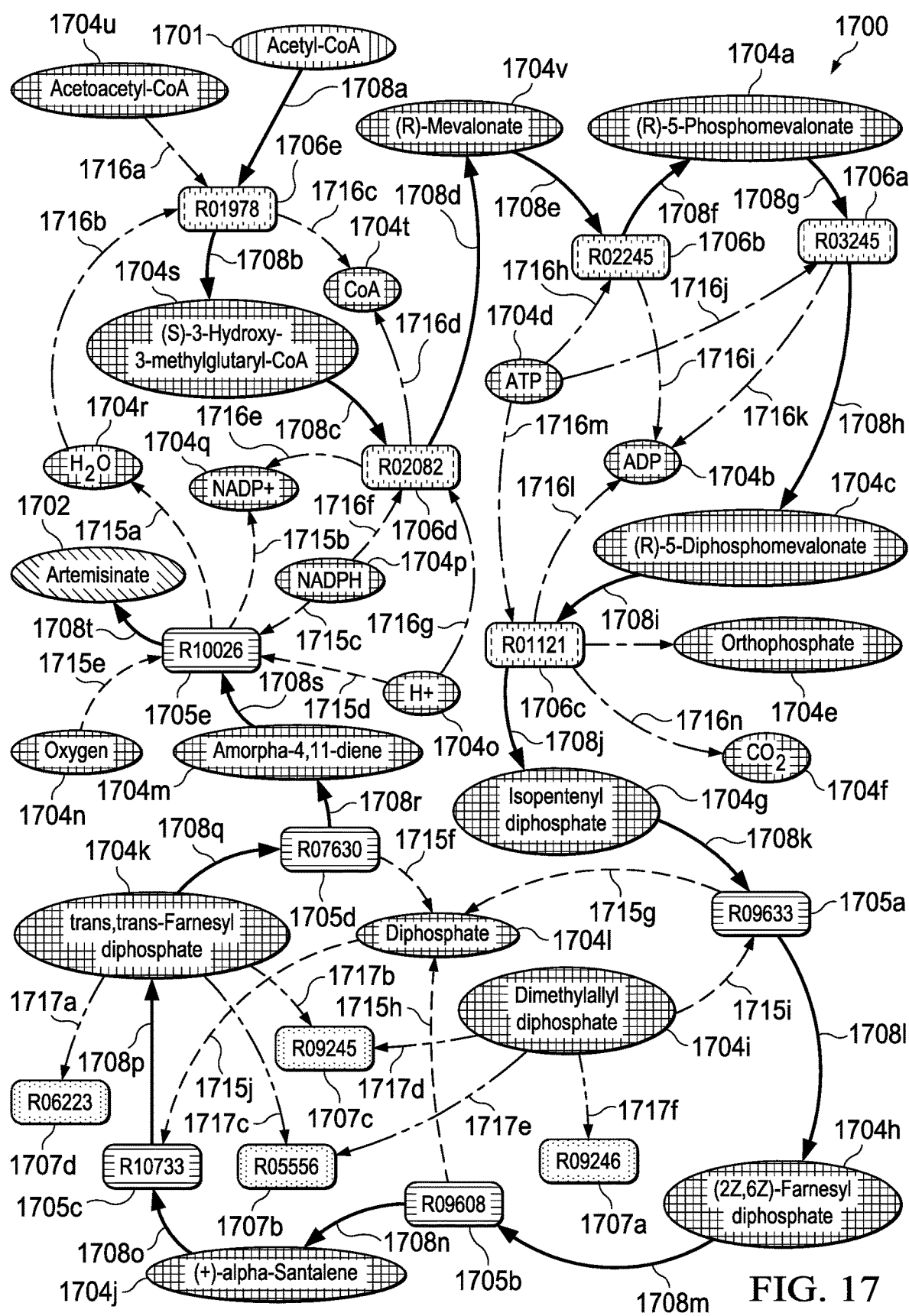
FIG. 17 is the present invention display of a pathway-level graph generated in MRE of the top-ranked pathway for the production of artemisinic acid from acetyl-CoA in yeast.

In FIGS. 16 and 17, two routes are shown for the production of artemisinic acid from acetyl-CoA in yeast. FIG. 16 is a known route and FIG. 17 is an MRE top-ranked route. To see if MRE could recover this engineered pathway, MRE was applied to explore pathways for the production of artemisinic acid from acetyl-CoA in yeast. It was found that one of the top-ranked pathways that MRE generated was this known heterologous pathway (FIG. 16). Interestingly, the pathway that MRE identified as the top candidate (FIG. 17) was slightly different from the previously engineered pathway. The difference lies in how isopentenyl pyrophosphate (IPP) is converted into farnesyl pyrophosphate (FPP). In the top-ranked path, IPP is first converted into (2Z,6Z)-farnesyl diphosphate (Z,Z-FPP). This route is chosen because IPP is a precursor of a thermodynamically highly favorable native reaction, and the conversion reaction from IPP to Z,Z-FPP is much more favorable than that from IPP to FPP, enabling a higher fraction of IPP to be utilized in the route. By using Z,Z-FPP as the precursor, this route introduces three foreign carbon-oxygen lyases to form FPP. FMM, Metabolic tinker and PHT were not able to find any pathways. XTMS found a partial pathway that converts FPP into artemisinic acid, albeit it is for the *E. coli* chassis.

In the known route (1600) shown in FIG. 16, the acetyl-CoA starting material (1601) is converted to desired product artemisinic acid (1602) via reaction route 1608a-1608p. The route includes endogenous reactions 1606a-1606f shown along arrows 1616a-1616p (which indicate paths native to the host) and heterologous reactions 1605a, 1605b shown along arrows 1615a-1615f (which indicate paths foreign to the host). Intermediate metabolites produced or used by these reactions are shown by 1604a-1604t. There are three competing endogenous reactions (nodes 1607a, 1607b, 1607c and arrows 1617a, 1617b, 1617c) that compete with desire route (1608*l*-1608*m*) for the intermediate metabolite trans, trans, farnesyl diphosphate (1604*k*). In an MRE generated pathway level graph, starting, ending and intermediate compounds are shown in red, green and yellow, respectively, the top-ranked route is seen in dark blue, and native, foreign and competing reactions and paths are shown in purple, cyan and gray respectively, to allow a user to quickly identify the components by color in each route.

In an MRE top-ranked route (1700) shown in FIG. 17, the acetyl-CoA starting material (1701) is converted to desired product artemisinic acid (1702) via reaction route 1708*a*-1708*t*. The route includes endogenous reactions 1706*a*-1706*e* shown along arrows 1716*a*-1716*n* (which indicate paths native to the host) and heterologous reactions 1705*a*-1705*e* shown along arrows 1715*a*-1715*i* (which indicate paths foreign to the host). Intermediate metabolites produced or used by these reactions are shown by 1704*a*-1704*v*. There are three competing endogenous reactions (nodes 1707*a*, 1707*b* 1707*c* and arrows 1717*e*, 1717*f*, 1717*g*) that compete with desire route (1708*m*-1708*n*) for the intermediate metabolite dimethylallyl diphosphate (1704*i*), and three competing endogenous reactions (nodes 1707*b*, 1707*c*, 1707*d* and arrows 1717*a*, 1717*b*, 1717*c*) that compete with desire route (1708*p*-1708*q*) for the intermediate metabolite trans, trans, farnesyl diphosphate (1704*k*). In an MRE generated pathway level graph, starting, ending and intermediate compounds are shown in red, green and yellow, respectively, the top-ranked route is seen in dark blue, and native, foreign and competing reactions and paths are shown in purple, cyan and gray, respectively, to allow a user to quickly identify the components in each route.

The present invention, MRE, is an open-access biosynthesis design tool, that searches for promising metabolic routes for a given biosynthesis specification and suggests exogenous enzymes for heterologous biosynthesis pathways based on the infrastructure of an endogenous metabolic system. The present invention relies on the data sources (mainly KEGG) to mine verified metabolic reactions and to search for biosynthesis routes based on them. Indeed, while painstaking effort has resulted in a large collection of annotated metabolic reaction data, among the 9910 reactions in the KEGG REACTION database (Release 76.0), 1272 reactions with no EC numbers were found, 1079 with partial EC numbers were found and 2170 with no annotations for associated genes were found. The number of verified reactions in KEGG is expected to increase over time which would alleviate any issues related to a lack of verified reactions. Other metabolic reaction databases, such as Rhea, may also be integrated.

Several existing tools took an approach to expand a list of metabolic parts in hand by defining specific transformation rules, albeit such rules can be subjective. To design biosynthesis systems, this approach relies on the prediction of metabolic parts with specific metabolic activities, which may or may not exist. Thus, the design of biosynthesis systems via this top-down approach may require the de novo design of unnatural proteins to achieve specific metabolic activities. MRE was developed to suggest actual enzymes for heterologous pathways. Thus, it takes a complementary, bottom-up approach in which a biosynthesis system is designed by using well-characterized metabolic parts. To this end, only verified reactions were used.

Here, by using the biosynthesis of a range of high-value natural products as a case study, it has shown that MRE can suggest promising heterologous biosynthesis pathways and provide useful information to pinpoint bottlenecks of pathways. With the host-dependent competition-based pathway ranking scheme, along with the suggestion of foreign enzymes with competing endogenous reactions, MRE offers novel insights into the design and optimization of heterologous biosynthesis systems.

While the invention is susceptible to various modifications and alternative forms, specific embodiments thereof have been shown by way of example in the drawings and are herein described in detail. For example, the user-interface example pages shown in FIGS. 1-5 do not itemize or describe in detail the dimensions, shapes, sizes, inputs or outputs, or exact specification of the identified items (e.g. user input, summary tables, etc.), which are all understood to exist and be within the scope of the invention as described and claimed.

Furthermore, size and shapes of display pages, input fields and linked data are not described in detail, but such details are understood to be varied or modifiable while still complying with the scope of the invention set forth herein and covered by the claims. It should be understood, however, that the description herein of specific embodiments is not intended to limit the invention to the particular forms disclosed, but on the contrary, the intention is meant to cover all modifications, equivalents, and alternatives falling within the spirit and scope of the invention as defined by the appended claims.

What is claimed is:

1. A method of determining and displaying suitable heterologous biosynthesis pathways to produce a target product in a specified host organism from a selected starting material, comprising the steps of:

selecting and inputting user input data that includes designation of a host organism, a starting compound, and a desired target product into the pathway computer system;

searching for one or more possible heterologous pathways based on competing endogenous reactions in a given host organism;

determining one or more suitable heterologous biosynthesis pathways from the starting compound to achieve the desired target product based on the competing endogenous reactions in the given host organism, thermodynamic criteria for the foreign reaction according to competing native reactions, and thermodynamic criteria involved in one or more reactions;

dynamically ranking suitable heterologous biosynthesis pathways from the starting compound to achieve the desired target product by an endogenous pathway score, wherein dynamically ranking includes the integration of new reactions into the endogenous metabolic system, and said endogenous pathway score is the sum of all reaction weights in a given pathway for the reaction, pathways from the source compound to the target product, number of reactions that are native and foreign to the host organism, and whether the reactions are endogenous to the host;

generating a graph of a predetermined number of most suitable heterologous biosynthesis pathways that shows reactions steps and metabolites, as well as competing endogenous reactions, displaying graphically one or more suitable heterologous biosynthesis pathways from the starting compound to the target product, in which vertices on the graph represent metabolites and arrow edges on the graph represent chemical transformations via verified metabolic reactions, said graphical display has color coding of vertices and edges to indicate starting and ending compounds, and which reactions are native or foreign to the host organism, and the graphical display includes a variation of the width of the arrow edges to indicate the value of the Gibbs energy, or strength, of the reaction path, wherein the graphical display includes dynamically changing the display based on the placement of a computer pointer over nodes or edges of compound names or the reaction Gibbs energy; and, utilizing the data supplied in the graphical display to select a preferred heterologous biosynthesis pathway for a specified chemical transformation.

2. The method of claim 1 wherein said user input data selected and input may also include selecting the number of reactions per pathway or the number of pathways.

3. The method of claim 1 wherein said user input data may also include selecting one or more compounds to exclude from the suitable pathway designation.

4. The method of claim 1 wherein said determining step may include providing the user with possible suggestions on one or more heterologous enzymes that may increase the favorability of the reaction pathway.

5. The method of claim 1 further comprises the step of:
identifying and suggesting foreign enzymes that may be used to catalyze the desired foreign reactions to increase the efficiency in achieving the target end product.

6. The method of claim 1 wherein said predetermined number of suitable heterologous biosynthesis pathways on the generated graph is between ten and thirty.

7. The method of claim 1 further comprising the steps of:
displaying a table of the specific reaction steps for the route with the reaction identification, reaction formula, whether the reaction is native to the host, the Gibbs energy of the reaction step, the native enzymes, potential foreign enzymes and data for the competing endogenous reactions, and selecting one or more enzymes from the table to generate and display enzyme data relating to the selected enzyme.

8. A method of determining and displaying suitable heterologous biosynthesis pathways to produce a target product in a specified host organism from a selected starting material, comprising the steps of:
selecting and inputting user input data that includes designation of a host organism, a starting compound, and a desired target product into the pathway computer system;

searching for one or more possible heterologous pathways with based on competing endogenous reactions in a given host organism;

determining one or more suitable heterologous biosynthesis pathways from the starting compound to achieve the desired target product based on the competing endogenous reactions in the given host organism;

identifying and suggesting foreign enzymes that may be used to catalyze the desired foreign reactions to increase the efficiency in achieving the target end product;

dynamically ranking suitable heterologous biosynthesis pathways from the starting compound to achieve the desired target product by an endogenous pathway score, wherein dynamically ranking includes the integration of new reactions into the endogenous metabolic system, and said endogenous pathway score is the sum of all reaction weights in a given pathway for the reaction, pathways from the source compound to the target product, number of reactions that are native and foreign to the host organism and whether the reactions are endogenous to the host;

generating a graph of a predetermined number of most suitable heterologous biosynthesis pathways that shows reactions steps and metabolites, as well as competing endogenous reactions;

displaying graphically one or more suitable heterologous biosynthesis pathways from the starting compound to the target product, in which vertices on the graph represent metabolites and arrow edges on the graph represent chemical transformations via verified metabolic reactions, said graphical display has color coding of vertices and edges to indicate starting and ending compounds and which reactions are native or foreign to the host organism, and the graphical display includes a variation of the width of the arrow edges to indicate the value of the Gibbs energy, or strength, of the reaction path, wherein the graphical display includes dynamically changing the display based on the placement of a computer pointer over nodes or edges of compound names or the reaction Gibbs energy; and utilizing the data supplied in graphical display to select a preferred heterologous biosynthesis pathway for a specified chemical transformation.

9. The method of claim 8 wherein said determining step uses thermodynamic criteria for the foreign reaction based on competing native reactions and thermodynamic criteria involved in one or more reactions.

10. The method of claim 8 further comprising the steps of:
displaying a table of the specific reaction steps for the route with the reaction identification, reaction formula, whether the reaction is native to the host, the Gibbs energy of the reaction step, the native enzymes, potential foreign enzymes and data for the competing endogenous reactions; and selecting one or more enzymes from the table to generate and display enzyme data relating to the selected enzyme.

* * * * *